US007091332B1

(12) United States Patent
Bramley et al.

(10) Patent No.: US 7,091,332 B1
(45) Date of Patent: Aug. 15, 2006

(54) TREATMENT OF STAPHYLOCOCCUS INFECTIONS

(75) Inventors: A. John Bramley, Hinesburg, VT (US); Karen I. Plaut, Westford, VT (US); David Kerr, Charlotte, VT (US)

(73) Assignee: University of Vermont, Burlington, VT (US)

( * ) Notice: Subject to any disclaimer, the term of this patent is extended or adjusted under 35 U.S.C. 154(b) by 0 days.

(21) Appl. No.: 09/698,579

(22) Filed: Oct. 27, 2000

Related U.S. Application Data

(62) Division of application No. 09/337,079, filed on Jun. 21, 1999, now abandoned.

(60) Provisional application No. 60/090,175, filed on Jun. 22, 1998.

(51) Int. Cl.
*C07H 21/04* (2006.01)

(52) U.S. Cl. .................................................. 536/23.7

(58) Field of Classification Search ................ 536/23.7
See application file for complete search history.

(56) References Cited

U.S. PATENT DOCUMENTS

| 4,931,390 A |   | 6/1990  | Recsei          |
| 5,011,772 A |   | 4/1991  | Recsei          |
| 5,124,145 A |   | 6/1992  | Sordillo et al. |
| 5,189,015 A |   | 2/1993  | Höök et al.     |
| 5,234,684 A |   | 8/1993  | Sordillo et al. |
| 5,342,612 A |   | 8/1994  | Daley et al.    |
| 5,607,919 A |   | 3/1997  | Bojsen et al.   |
| 5,824,869 A | * | 10/1998 | Broekaert et al. |
| 6,028,051 A |   | 2/2000  | Climo et al.    |
| 6,204,020 B1 | * | 3/2001 | Ladner et al.   |

FOREIGN PATENT DOCUMENTS

| EP | 0 359 873    | 9/1988    |
| EP | 0 759 473    | 8/1995    |
| WO | WO 87/06264  | 10/1987   |
| WO | 96/35793     | * 11/1996 |
| WO | WO 96/35793  | 11/1996   |
| WO | WO 99/05289  | 2/1999    |

OTHER PUBLICATIONS

Houdebine, et al., *Journal of Biotechnology*, "Production of Pharmaceutical Proteins from Transgenic Animals", 34:269-287, 1994.
Mullins, et al., *Hypertension*, "Transgenesis in Nonmurine Species," 22: 630-633, 1993.
Wall, et al., *J. Dairy Sci.*, "Transgenic Dairy Cattle: Genetic Engineering on a Large Scale," 80:2213-2224.
Archer, et al., "Human Growth Hormone (hGH) Secretion in Milk of Goats After Direct Transfer of the hGH Gene into the Mammary Gland by Using Replication-Defective Retrovirus Vectors", *Proc. Natl.Acad. Sci.* 91: 6840-44, Jul. 1994.
Auldist, et al., "Changes in the Composition of Milk from Healthy and Mastitic Dairy Cows During the Lactation Cycle", *Aust. J. Exp. Agricul.* 35: 427-36, 1995.
Auldist, et al., "Effect of Somatic Cell Count and Stage of Lactation on the Quality and Storage Life of Ultra High Temperature Milk", *J. Dairy Res.* 63: 377-386, 1996.
Barbano, et al., "Influence of Milk Somatic Cell Count and Milk Age on Chesse Yield", *J. Dairy Sci.* 74: 369-88, 1991.
Bramley, et al., "Effects of Lysostaphin on *Staphylococcus aureus* Infections of the Mouse Mammary Gland", *Research in Veterinary Science*, 49:120-21; 1990.
Bramley, et al., "Reviews of the Progress of Dairy Science: Mastitis Control—Progress and Prospects" *Journal of Dairy Research*, 51, 481-512, 1984.
Chandler, "Experimental Bacterial Mastitis in the Mouse", *J. Med. Microbiol.* 3: 273-82, 1970.
Chomczynski, et al., "Single-Step Method of RNA Isolation by Acid Guanidinium Thiocyanate-Phenol-Chloroform Extraction", *Anal. Biochem.* 162: 156-59, 1987.
Craven, et al., "Phagocytosis of *Staphylococcus aureus* by Bovine Mammary Gland Macrophages and Intracellular Protection from Antibiotic Action in Vitor and In Vivo", *J. Dairy Res.* 51: 513-23, 1984.
Craven, et al., "Antibiotic Activity Against Intraleukocytic *Staphylococcus aureus* in Vitro and In Experimental Mastitis in Mice", *Am. J. Vet. Res*, 44:(4), 709-12, 1983.
Daley, et al., "Lysostaphin: Immunogenicity of Locally Administered Recombinant Protein Used in Mastitis Therapy", *Veterinary Immunology and Immunopathology*, 31:301-12, 1992.
Derbyshire, et al., "Immunization Against Experimental *Staphylococcal mastitis* in the Goat by the Intramammary Infusion of Cell-Toxoid Vaccine" *Res. Vet. Sci.*, 10:559-64, 1969.

(Continued)

*Primary Examiner*—Mark Navarro
(74) *Attorney, Agent, or Firm*—Brenda Herschbach Jarrell; Choate, Hall & Stewart, LLP

(57) ABSTRACT

The present invention relates to an improved approach for the treatment of microbial infections in mammals. Specifically, the invention provides methods and reagents for expressing in mammalian cells proteins that have antimicrobial activity. The invention provides both genes which have been modified to allow expression and preferably secretion of active protein in desired mammalian cells or tissues, and methods of introducing such modified genes into desired mammalian cells and/or tissues. Most specifically, genes encode anti-staphylococcal proteins are delivered to mammalian cells and/or tissues by methods of gene delivery, including gene therapy and the production of transgenic animals, for the treatment of mastitis in ruminant animals.

26 Claims, 29 Drawing Sheets

OTHER PUBLICATIONS

Ebert, et al., "Transgenic Production of a Variant of Human Tissue-Type Plasminogen Activator in Goat Milk: Generation of Transgenic Goats and Analysis of Expression", *Bio/Technology*, 9: 835-38, 1991.

Gordon, et al., "Production of Human Tissue Plasminogen Activator in Transgenic Mouse Milk", *Bio/Technology*, 5: 1183-87, 1987.

Harmon, et al., "Concentration of Lactoferrin in Milk of Normal Lactating Cows and Changes Occurring during Mastitis" *Am. J. Vet. Res.*36: 1001-1007, 1975.

Heinrich, et al., "The Molecular Organization of the Lysostaphin Gene and its Sequences Repeated in Tandem", *Mol. Gen Genet*, 209:563-69, 1987.

Jacob, et al., "Potential Therapeutic Applications of Magainins and Other Antimicrobial Agents of Animal Origin", *Ciba. Found. Symp.* 186: 197-216, discussion, 216-23, 1994.

Kagan, et al., "Defensins: A Family of Antimicrobial and Cytotoxic Peptides", *Toxicology*, 87: 131-49, 1994.

Kerr, et al., "Expression of Gene-gun Injected Plasmid DNA in the Ovine Mammary Gland and In Lymph Nodes Draining the Injection Site" Animal Biotechnology 7:33-45, 1996.

Klei, et al., "Effects of Milk Somatic Cell Count on Cottage Cheese Yield and Quality", *J. Dairy Sci.* 81:1205-13, 1998.

Kossaibati, et al., "Incidence of Clinical Mastitis in Dairy Herds in England", *Vet. Rec.* 143:649-53, 1998.

Krimpenfort, et a., "Generation of Transgenic Dairy Cattle Using 'In Vitro' Embryo Production" *Bio/Technology*, 9: 844-47, 1991.

Liang, et al., "Molecular Cloning and Nucleotide Sequence of the β-Lytic Protease Gene from Achromobacter Lyticus" *Journal of Bacteriology*, 172(11):6506-11; 1990.

Maga, et al., "Antimicrobial Properties of Human Lysozyme Transgenic Mouse Milk", *J. Food Prot.* 61: 52-56, 1998.

Maga, et al., "The Effect of Mammary Gland Expression of Human Lysozyme on the Properties of Milk From Transgenic Mice", *J. Dairy Sci.* 78: 2645-52, 1995.

Myllys, et al., "Bovine Mastitis in Finland in 1988 and 1995—Changes in Prevalence and Antimicrobial Resistance", *Acta Vet. Scand.* 39: 119-126, 1998.

Nickerson, et al., "Symposium: Mastitis in Dairy Heifers, Mastitis in Dairy Heifers: Initial Studies on Prevalence and Control", *J Dairy Sci*, 78:1607-18, 1995.

Nuijens, et al., "Characterization of Recombinant Human Lactoferrin Secreted in Milk of Transgenic Mice" *J. of Biol. Chemi.*, 272 (13): 8802-07, 1997.

Oldham, et al., "Lysostaphin: Use of a Recombinant Bactericidal Enzyme as a Mastitis Therapeutic", *J. Dairy Sci.*, 74:4175-82, 1991.

Platenburg, et al., "Expression of Human Lactoferrin Milk of Transgenic Mice", *Transgenic Res.* 3:99-108, 1994.

Plaut, et al., "Integration of the IacZ Gene into the Mammary Gland Using an Adenovirus Vector", *J. Dairy Sci.*, 80:1, 1997.

Recsei, et al., "Cloning, Seguence, and Expression of the Lysostaphin Gene From Staphylococcus Simulans", *Proc. Natl. Acad. Sci., USA*, 84: 1127-31, 1987.

Reiter, B., "Review of the Progress of Dairy Science: Antimicrobial Systems in Milk", *J. Dairy Res.* 45: 131-47, 1978.

Schindler, et al., Lysostaphin: A New Bateriolytic Agent For the *Staphyloccus. Proc. Natl. Acad. Sci. U.S.A.* 51:414-421, 1964.

Schnieke, et al., "Human Factor IX Transgenic Sheep Produced by Transfer of Nuclei From Transfected Fetal Fibroblasts", *Science*, 278:2310-33, 1997.

Shockman, et al., "Stucture, Function, and Assembly of Cell Walls of Gram-Positive Bacteria", *Annu. Rev. Microbiol.* 37: 501-27, 1983.

Sutra, et al., "Virulence Factors Involved in the Pathogenesis of Bovine Intramammary Infections Due to *Staphylococcus aureaus*", *J. Med. Microbiol.* 40: 79-89, 1994.

Takahashi, et al., "Nonspecific Antibacterial Factors in Milk from Cows Immunized with Human Oral Bacterial Pathogens", *J. Dairy Sci.* 75:1810-20, 1992.

Thumm, et al., "Studies on Prolysostaphin Processing and Characterization of the Lysostaphin Immunity Factor (Lif) of *Staphulococcus Simulans Biovar Staphylolyticus*" *Molecular Microbiology*, 26(6), 1251-65, 1997.

Verdi, et al., "Variability in True Protein, Casein, Nonprotein Nitrogen, and Proteolysis in High and Low Somatic Cell Milks", *J. Dairy Sci.* 70: 230-42, 1987.

Wall, et al., "High-Level Synthesis of a Heterologous Milk Protein in the Mammary Glands of Transgenic Swine", *Proc. Natl. Sci USA*, 88: 1696-1700, 1991.

Watson, et al., "Field Trial of *Staphyloccocal Mastistis* vaccine in Dairy Herd: Clinical Subinical, and Microbiological Assessments" Australian Veterinary Journal, Dec. :74(6):447-450, 1996.

Williamson, et al., "Expression of Lysostaphin in the Milk of Transgenic Animals to Combat *Staphylococcal Mastistis*", *J. Appl Bacterial.* 67:6, xxi, 1986.

Williamson, et al., "Expression of the Lysostaphin Gene of *Staphylococcus Simulans* in a Eukaryotic System", *Applied and Environment Microbiology*, 60:3, 771-76, Mar., 1994.

Wilson, et al., "Bovine Mastitis Pathogens in New York an Pennsylvania: Prevalence and Effects on Somatic Cell Count and Milk Production", *J. Dairy Sci.* 80: 2592-98, 1997.

Wright, et al., "High Level Expression of Active Human Alpha-1-Antitrypsin in the Milk of Transgenic Sheep", *Bio/Technology*, 9:830-34, 1991.

Yamada, et al., "An Autolysin Ring Associated with Cell Separation of *Staphylococcus aureus*", *J. Bacterial.* 178: 1565-71, 1996.

Yancey, et al., "Activiy of Antibiodics Against *Staphylococcus aureus* Within Polymorphonuclear Neutrophils", *Eur. J. Clin. Microbiol. Infect. Dis.* 10:107-113, 1991.

Yarus, et al., "Production of Active Bovine Trachael Antimicrobial Peptide in Milk of Transgenic Mice", *Proc. Natl. Acad. Sci. USA*, 93, 14118-21, Nov., 1996.

Zavizion, et al., "Effects of *Staphylococcus aureus* Toxins on the Growth of Bovine Mammary Epithelial Cells (MAC-T) in Culture", *J. Diary Sci.*, 78, 277-84, 1995.

* cited by examiner pCMLEM (Williamson et al. 1994)

pCMV-LYS pCMV-hGH-Lys pCMV-hGH-Lys-ΔGly2 pCMV-hGH-Lys-ΔGly1-ΔGly2

FIG.11-1

A. ORIGIN

```
  1 ccggaactct tgaatgttta gtttgaaaa ttccaaaaaa aaactactt tcttaatatt
 61 gattcatatt attttaacac aatcagttag aatttcaaaa atcttaaagt caattttga
121 gtgtgtttgt atatttcatc aaaatcaatc aatattattt tactttcttc atcgttaaaa
181 aatgtaatat ttataaaaat atgctattct cataaatgta ataataaatt aggaggtatt
241 aaggttgaag aaaacaaaaa acaattatta tacgagacct ttagctattg gactggtac
301 atttgcctta gcatctattg tttatgggag gattcaaaat gaaacacatg cttctgaaaa
361 aagtaatatg gatgtttcaa aaaagtagc cttcaaaagc tgaagtagag acttcaaaag cccagtaga
421 aaatacagct gaagtagaga atacagctga agtagagact tcaaagctc cagtagaaaa
481 ttcaaaagct ccagtagaaa cagctcc ggtagaaaat acagctgaag tagagactttc
541 tacagctgaa gtagagactt caaagctcc ggtagaaaat acagctgaag tagagacttc
601 aaaagccca gtagaaaata cagctgaagt agagacttca aagccctgg ttcaaaatag
661 aacagcttta agagctgcaa cacatgaaca ttcagcacaa tggttgaata attacaaaaa
721 aggatatggt tacggtcctt atccattagg tataaatggc ggtatgcact acggagttga
```

```
 781 tttttttatg aatatttggaa caccagtaaa agctatttca agcggaaaaa tagttgaagc
 841 tggttggagt aattacggag gagtaatca aataggtctt attgaaaatg atggagtgca
 901 tagacaatgg tatatgcatc taagtaaata taatgttaaa gtaggagatt atgtcaaagc
 961 tggtcaaata atcggttggt ctggaagcac tggttattct acagcaccac atttacactt
1021 ccaaagaatg gtaattcat tttcaaattc aactgccaa gatccaatgc ctttcttaaa
1081 gagcgcagga tatggaaaag caggtggtac agtaactcca acgccgaata caggttggaa
1141 aacaaacaaa tatgcacac tatataaatc agagtcagct agcttcacac ctaatacaga
1201 tataataaca agaacgactg gtccatttag aagcatgccg cagtcaggag tcttaaaagc
1261 aggtcaaaca atcattatg atgaagtgat gaaacaagac ggtcatgttt gggtaggtta
1321 tacaggtaac agtggccaac gtatttactt gcctgtaaga acatggaata aatctactaa
1381 tactttaggt gtctttggg gaactataaa gtgagcgcgc ttttatataa cttatatgat
1441 aattagagca aataaaatt tttctcatt cctaaagttg aagctt
```

FROM FIG.11-1

FROM FIG.11-2

B.
BASE COUNT
ORIGIN

```
  1 gctgcaacac atgaacattc agcacaatgg ttgaataatt acaaaaaagg atatggttac
 61 ggtccttatc cattaggtat aaatggcggt atgcactacg gagttgattt ttttatgaat
121 attggaacac cagtaaaagc tatttcaagc ggaaaaatag ttgaagctgg ttgggataat
181 tacggaggag gtaatcaaat aggtcttatt gaaaatgatg gagtgcatag acaatggtat
241 atgcatctaa gtaaatataa tgttaaagta ggagattatg tcaaagctgg tcaaataatc
301 ggttggtctg gaagcactgg ttattctaca gcaccacatt tacacttcca aagaatggtt
361 aattcatttt caaattcaac tgcccaagat ccaatgcctt tcttaaagag cgcaggatat
421 ggaaaagcag gtggtacagt aactccaacg ccgaatacag gttggaaaac aaacaaatat
481 ggcacactat ataaatcaga gtcagctagc ttcacaccta atacagatat aataacaaga
541 acgactggtc cattagaag catgccgcag tcaggagtct taaaagcagg tcaaacaatt
601 cattatgatg aagtgatgaa acaagacggt catgtttggg taggttatac agttaacagt
661 ggccaacgta ttttacttgcc tgtaagaaca tggaataaat ctactaatac ttaggtgtt
721 ctttgggggaa ctataaagtg a
```

FIG. 12

"MKKTKNNYYTRPLAIGLSTFALASIVYGGIQNETHASEKSNMDV
SKKVAEVETSKAPVENTAEVETSKAPVENTAEVETSKAPVENTAE
VETSKAPVENTAEVETSKALVQNRTALRAATHEHSAQWLNNYKKG
YGYGPYPLGINGGMHYGVDFFMNIGTPVKAISSGKIVEAGWSNYGGGNQIGLIENDGV
HRQWYMHLSKYNVKVGDYVKAGQIIGWSGSTGYSTAPHLHFQRMVNSFSNSTAQDPMP
FLKSAGYGKAGGTVTPTPNTGWKTNKYGTLYKSESASFTPNTDIITRTTGPFRSMPQS
GVLKAGQTIHYDEVMKQDGHVWVGYTGNSGQRIYLPVRTWNKSTNTLGVLWGTIK"

FIG.13

ORIGIN

```
  1 gccgcaacac atgaacattc agcacaatgg ttgaataatt acaaaaaagg atatggttac
 61 ggcccttatc cattaggtat aaatggcggt atgcactacg gagttgattt ttttatgaat
121 attggaacac cagtaaaagc tatttcaagc ggaaaaatag ttgaagctgg ttgggtaat
181 tacggaggag gtaatcaaat aggtcttatt gaaaatgatg gagtgcatag acaatggtat
241 atgcatctaa gtaaatataa tgttaaagta ggagattatg tcaaagctgg tcaaataatc
301 ggttggtctg gaagcactgg ttattctaca gcaccacatt tacacttcca aagaatggtt
361 aactcattt cacagtcaac tgccaagat ccaatgcctt tcttaaagag cgcaggatat
421 ggaaaagcag gtggtacagt aactccaacg ccgaatacag gttggaaaac aaacaaatat
481 ggcacactat ataatcaga gtcagctagc ttcacaccta atacagatat aataacaaga
541 acgactggtc catttagaag catgccgcag tcaggggtct taaaagcagg tcaaacaatt
601 cattatgatg aagtgatgaa acaagacggt catgtttggg taggttatac aggtaacagt
661 ggccaacgta tttacttgcc tgtgagaaca tggcagaagt ctactaatac tctgggtgtt
721 ctgtggggaa ctataaagtg a
```

FIG.14-1

A. ORIGIN

```
  1 tgtgtgcgtg ctcccattcg ttcatgctcg ccacgcgcac ggccgcgctt tgcgacgcga
 61 tcgcgcaccg tgtgaaccgc attgaggaat ggccgttcgg caagcgcatg tacggcctcg
121 atttgaacgt gcgtcgcacg acagcgtcgc gcccgcggtc agagtccggc gcccgcggta
181 tacggacagc gatcgcgcg tccgccgatg acgaacggtc gtgcgcgtca gtcgcatgcg
241 ccgctcgccg ctggcgttcc ggcttcgcgg gcgcagcgcg gtccaccact cttcaaacgt
301 ctttctcggg agcagcatat gaagaagatt tccaaggcgg gactggggct ggcgctggtg
361 tgcgcgctgg cgacgatcgg cggcaacgca gcgcgcaggg ccacgctca gcgcgaggo
421 tctggtgtat tctacgacga gatgttcgac ttcgacatcg atgcgcatct ggccaagca
481 gcgccgcatc tgcacaagca ctcggaagag atctcgcact gggccggcta cagcgggatc
541 agccgaagtg ttgatcgcgc ctggcgcaag gcagagcgcg cggtcacgcc aagcgcgcga
601 cgaatcgtcc gttcggcaag ctgccgcgcg ccgacgcgtt cggcgcgcag acccgcgagg
661 tcgcgctggc gctgccgcag tcgctgtacg agcgcgatcc cgacgcgcca aggggccggt
721 gacgctggcc cgcgccaatc cgctgcaggc gctgttcgag cgttccggcg acaacgagcc
781 ggcggccgcg ctgccgggcg acggcgagtt ccagctggtc tacggccgcc tgttcaacga
```

FROM FIG.14-1

```
 841 accgcgccag gccaaggcgg cttcggaccg cttcgccaag gccggcccgg acgtgcagcc
 901 gtgtcgccca acggcctgct gcagttcccc ttcccgcgcg ggccagctg gcatgtcggc
 961 gggcccacca ccaacaccgg ctcgggcaat tacccgatgt cgtcgctgga catgtcgcgc
1021 ggcggcggct gggcagcaa ccagaacggc aactgggtgt cggcctcggc cgcggctcg
1081 ttcaagcgcc actcttcgtg cttcgcggag atcgtgcaca ccggcggctg gtcgacgacc
1141 tactaccacc tgatgaacat ccagtacaac accggcgcca acgtgtcgat gaacaccgcc
1201 atcgccaacc cggccaaca ccaggcgcag ggcgtgtgca acggcggcca gtcgaccggc
1261 ccgcacgagc attggtcgtt gaagcagaac ggcagcttct accacctcaa cggcacctac
1321 ctgtcgggct atcgcatcac cgcgaccggc agcagctatg acaccaactg cagccggttc
1381 tatctgacca agaacggcca gaactactgc taccgcgtt acgtcaaccc gggcccgaac
1441 tgaggctcgc cgcgtgcgtt gccccgcgtcc tcaagcgccc cacgcgcggg gcgcgggcac
1501 cggccgggtc aggtcgaatt
```

"MKKISKAGLGLALVCALATIGGNAARRATAQRRGSGVFYDEMFD
FDIDAHLAKHAPHLHKSEEISHWAGYSGISRSVDRADGAAERAVTPSARRIVRS
ASWRAPTASARRPARSRWRCASRCTSAIPTRQGAGDAGPRQSAAGAVRAFRRQRAG
GRAARRRRVPAGLRPPVQRTAPGQGGFGPLRQGRPGRAAVSPNGLLQFPFPRGASWHVG
GAHTNTGSGNYPMSSLDMSRGGGWGSNQNGNWVSASAAGSFKRHSSCFAEIVHTGG
WSTTYYHLMNIQYNTGANVSMNTAIANPANTQAQALCNGGQSTGPHEHWSLKQNGSFYH
LNGTYLSGYRITATGSSYDTNCSRFYLTKNGQNYCYGYYVNPGPN"

FIG. 15-1

A.
ORIGIN

```
  1 gaaattcca aaaaaaacc tactttctta atattgattc atattatttt acacaatca
 61 gttagaattt caaaatctt aagtcaatt tttggtgtg tttgtatatt tcatcaaagc
121 caatcaatat tatttact tcttcatcgt taaaaaatgt aatatttata aaatatgct
181 attctcataa atgtaataat aaattaggag gtattaaggt tgaagaaaac aaaaaacaat
241 tattatacga caccttttagc tattggactg agtacatttg cttagcatc tattgtttat
301 gggggattc aaaatgaaac acatgcttct gaaaaagta atatggatgt ttcaaaaaaa
361 gtagctgaag tagagactc aaaacccca gtagaaaata cagctgaagt agagacttca
421 aaagctccag tagaaataca agctgaagta gagacttcaa aagctccagt agaaaataca
481 gctgaagtag agacttcaaa agctccagta agctccagta gaaaatacag ctgaagtaga gacttcaaaa
541 gctccggtag aaaatacagc tgaagtagag cccagtagaa ctccggtaga aatacagct
601 gaagtagaga cttcaaaagc ccagtagaa aatacagctg aagtagagac ttcaaaagct
661 ccagtagaaa atacagagct agtagagact tcaaaagctc cggtagaaaa tacagctgaa
721 gtagagactt caaaagcccc agtagaagt agagacttca aaagctccgg tagagactc aaagcctcca
781 gtagaaaata cagctgaagt agaaaagctc aaagctccgg tagaaaatac agctgaagta
841 ggagcttcaa aagctcccagt agaaaataca gctgaagtag agacttcaaa agccctggtt
```

```
 901 caaatagaa cagctttaag agctgcaaca catgaacatt cagcacaatg gttgaataat
 961 tacaaaaag gatatggtta cggtccttat ccattaggta taaatggcgg tatccactac
1021 gggttgatt ttttatgaa tattgaaca ccagtaaaag ctatttcaag cggaaaata
1081 gttgaagctg gttggagtaa ttacggagga ggtaatcaaa tagtcttat tgaaatgat
1141 gggtgcata gacaatggta tatgcatcta agtaaatata atgttaaagt aggagattat
1201 gtcaaagctg gtcaaataat cggttggtct ggaagcactg gttattctac agcaccacat
1261 ttacacttcc aaagaatggt taattcattt tcaaattcaa ctgccaaga tccaatgcct
1321 ttcttaaaga gcgcaggata tgaaaagca ggtggtacag taactccaac gccaataca
1381 ggttggaaaa caaacaaata tggcacacta tataaatcag agtcagctag cttcacacct
1441 aatacagata taataacaag aacgactggt ccatttagaa gcatgccgca gtcaggagtc
1501 ttaaaagcag gtcaaacaat tcattatgat gaagtgatga aacaagacgg tcatgtttgg
1561 gtaggttata caggtaacag tggccaacgt atttacttgc ctgtaagaac atggaataaa
1621 tctactaata ctttaggtgt tctttgggga actataaagt gagcgcgctt tttataaact
1681 tatatgataa ttagagcaaa taaaattt ttctcattcc taaagttgaa gcttttcgta
1741 atcatgtcat agcgtttcct gtgtgaaatt gcttagcctc acaattccac acaacatacg
1801 agccggaaca taaagtgcta agcct
```

FROM Fig. 15-1

"MKKTKNNYYTTPLAIGLSTFALASIVYGGIQNETHASEKSNMDV
SKKVAEVETSKPPVENTAEVETSKAPVENTAEVETSKAPVENTAE
VETSKAPVENTAEVETSKAPVENTAEVETSKAPVENTAEVETSKA
PVENTAEVETSKAPVENTAEVETSKAPVENTAEVETSKAPVENTA
EVETSKALVQNRTALRAATHEHSAQWLNNYKKGYGYGPYPLGINGGIHYGVDFFMNIG
TPVKAISSGKIVEAGWSNYGGGNQIGLIENDGVHRQWYMHLSKYNVKVGDYVKAGQII
GWSGSTGYSTAPHLHFQRMVNSFSNSTAQDPMPFLKSAGYGKAGGTVTPTPNTGWKTN
KYGTLYKSESASFTPNTDIITRTTGPFRSMPQSGVLKAGQTIHYDEVMKQDGHVWVGY
TGNSGQRIYLPVRTWNKSTNTLGVLWGTIK"

FIG.16-1

ORIGIN

```
   1 gatatcattt caaagacaga tattctaaag aaagatata ttttaaaaaa tgtgttgaa
  61 aaaattaaag aaattcacga tttgactat atatttattg atgtaccacc tactattaac
 121 tctgatttca ctaataatgc tgtttacgca agtgattaca tttaatggt atttcaaaca
 181 caacaatctg cttatgaaag tagtctttca tttgttaatt ttttaaggga tcgaaaaaaa
 241 gaatcagatt tatcatttga attggttggc gctgttccag tattaattaa aaaagtgga
 301 cgtgtagata aacagatatt agatatgtct aaatcagcat tttctgaagc actctttgag
 361 aaccagatat atcaaagaga aagaataaaa aaatttgccg ctgatggaat aaaagataaa
 421 gatatgcatg acaaaaagt tatatatatg tctacgaaga attttttagat attagttgat
 481 agagttagat taattgaagg tgagtgatat ttatgcagg atttttagat aacatagata
 541 catctgaggt aaaatatacg gaaaattata aaccggtatc taaagtacg actatgagag
 601 tggacactga tataaaaaaa agattaaatc aaatggcgtt agataaagat acatctataa
 661 aggctatagt tgatgaagtg ttaggagaat tttgaaaaa aaataagtat tagtatttta
 721 tataggctct atactattta ggactggtga taatcactag tcctattttt gatacaaaaa
 781 agcgccaatta tctctataat tagaagtatc ctaccaccaa taattaagga aataatgcgc
 841 ctatgtctaa tattatatca atcacccttg gaattaaaga taaaatatc actttgaag
 901 ataaggttga agaaagtata aagggaaaaa ttctttattt tactttgaa aattaataca
 961 ttctcccaag cgatgtaaac tttgcggaca cgaaaatacg aactttcta taatcaaaaa
1021 tggttttaaa aaatcatgtc ttacgatacc taaggtatcg gagaagccag cttatttaat
```

```
1081 attggaaaaa cagcgtttcc actgtaaaaa gtgctgcagt tatttcactg ctgaaacacc
1141 tgtcgttgag tggaattgct atatttctca aaacacacga ttagctgtgc tgaataagtc
1201 gatagacata cgttcgcaaa aatctgttgc tgaatcttgt catgtcagta attccacagt
1261 tactcgaata attaataaag ctgcttctca aatagctcaa acaccgttta aatatttacc
1321 ggaacacttg atgatggatg agttcaaaag cgttaaaaat gttgtcggta aatgagttt
1381 tatttatgca gatgcagtaa cacacgtat tattgatatt gtgcctgacc gcaggttatt
1441 tgctttgaaa aattattct accgttatcc tcttctgaa agaaatgtg tgaaagcagt
1501 gtctattgat atgtatgaac cttatatgc tttgatcaga gaagttttc ctaatgcaa
1561 aattctaata gttcatttcc atattgttca gtctttaat aaagccttga acatgactcg
1621 agtaacagtt atgaatagtt tcagaacaac tgcctg ctatacaaca agtacaagcg
1681 ttactggaag attctttaa aactgccttg aaaaatatag aatcaatag cgttgctcct
1741 aaacttcaaa cagctgttaa aacactaaga aagcacaata gaatgataag aaatactttt
1801 gaatacagta acttgaccaa cggttcactt gagggaataa atactaaaat aaagctgata
1861 cagagaatat cttttggtta tagaaatttt ggtgattac gcagtcgtat catttatgt
1921 acaaatcttt ttgcagctaa tccaaaaaaa gagatcaagc aactttatgc tgcttaatct
1981 ctgcgttta gctcaccagt cttatttgac agagagccaa taaattaac ggagggagaa
```

FROM FIG.16-1

```
2041 ggattcgaac caacgcaagc acatacatgc tcctaattaa taaaatata ttaatccct
2101 taatccagac ttggtatcc ctccacaagc attatttaat gctaatataa catatataac
2161 aacaaatgta aatatgtatt tataaggaaa aggatattaa aattattctg agttatataa
2221 ggtagtattc ataatcatcc taaagttgaa gtcgaaaagc ttcaactta ggaatgagaa
2281 aaaatttta tttgctctaa ttatcatata agtttataaa aagcgcgtc actttatagt
2341 tcccaaaga acacctaaag tattagtaga tttattccat gttcttacag gcaagtaaat
2401 acgttggcca ctgttacctg tataacctac ccaaacatga ccgtcttgtt tcatcacttc
2461 atcataatga attgtttgac ctgcttttaa tatctgtatt aggtgtgaag ctagctgact ctgatttata
2521 accagtcgtt cttgtatta tattgtttg tttccaacc tgtattcggc gttggagtta ctgtaccacc
2581 tagtgtgcca tatttgttg tttccaacc tctttaagaa aggcattgga tcttgggcag ttgaatttga
2641 tgcttttcca tatcctgcgc tctttaagaa aggcattgga tcttgggcag ttgaatttga
2701 aaatgaatta accattcttt ggaagtgtaa atgtggtgct gtagaataac cagtgcttcc
2761 agaccaaccg attatttgac cagctttgac ataatctcct actttaaacat tatattact
2821 tagatgcata taccattgtc tatgcactcc atcatttca ataagaccta tttgattacc
2881 tcctccgtaa ttactccaac cagcttcaac tattttccg cttgaaatag cttttactgg
2941 tgttccaata ttcataaaaa aatcaactcc gtagtgcata ccgccattta tacctaatgg
```

```
3001 ataaggaccg taaccatatc ctttttgta attattcaac cattgtgctg aatgttcatg
3061 tgttgcagct ctaaagctg ttctatttg aaccaggct ttgaagtct ctacttcagc
3121 tgtattttct actgggctt ttgaagtctc tacttcagct gtatttcta ccggagcttt
3181 tgaagtctct acttcagctg tattttctac tggagctttt gaagtctcta cttcagctgt
3241 attttctact ggggctttg aagtctcta ttcagctgta ttttctaccg gagcttttga
3301 agtctctact tcagctgtat ttttctactgg agcttttga gtctctactt cagctgtatt
3361 ttctactact gctttgaag tctctacttc agctgtattt tctaccggag cttttgaagt
3421 ctctacttca gctgtatttt ctaccggagc tttgaagtc tctacttcag ctgtattttc
3481 taccggagct tttgaagtct ctacttctct actggagctt ttgaagtctc
3541 tacttcagct gtattttcta ctggagcttt tgaagtctct acttcagctg tatttctac
3601 tggagctttt gaagtctcta cttcagctgt atttctact gggctttg aagtctctac
3661 ttcagctact ttttgaaa catccatat actttttca gaagcatgtg ttcatttg
3721 aatccctcca taaacaatag atgctaaggc aaatgtactc agtccaatag ctaaaggtct
3781 cgtataataa ttgttttttg tttcttcaa cctaatacc tcctaattta ttattacatt
3841 tatgagaata gcatattttt ataatatta catttttaa cgatgaagaa agtaaaataa
3901 tattgattga tttgatgaa atatacaaac acactcaaaa attgacttta agattttga
```

From FIG.16-3
To Fig.16-5

FIG.16-5

```
3961 aattctaact gattgtgtta aaataatatg aatcaatatt aagaaagtag gtttttttt
4021 ggaattttca aaactaaaca ttcaaggagtt cgaaggaatt gtgtttcaaa aaatgtctca
4081 ttacacacaa tctgcttctc attttgaata tagaaataac catcagaata atgtgcattt
4141 agtggcgta aaaaatgaaa cagtgaagt attagctgct tgtttactga ctgaggcacg
4201 ttgtttaaag ttctttaaat attctatac acatcgcggt ccagtcatga actttaaaga
4261 ccatggagtta gtcagatttt tttatgaaaa cttaacgacc tatctaaaaa agcaaaactg
4321 cttatatgtt ttaactgacc ctacctgtt agaaaatatt cgaagttgtg acggagaaat
4381 ccttgaatct tatgataacg aaactttat gaacgtgatg aatttattag gttaccgtca
4441 tcaagggttt actacaggtt atctctcaaac aagtcagatc agatggttgt cggtcttaaa
4501 cctagaaaat aaagatgaaa aacaattgtt aaaagaaatg gattatcaaa cacgccgtaa
4561 tattaagaaa acctatgaaa agtccgcgat ttatcaatta atgaaacaga
4621 tcgatttttt aaattattta aaatggctga agaaaaacat ggcttcaaat tcagagaaca
4681 aagttattttt gaaagaatgc agaaaacata cgctgataat agtatgttaa agctggctta
4741 catcgattta tagagacaca aaataaaga aaaccctaat tctaagaaaa acaaaaataa
4801 tattgaaaat attcaagcgg cattaaaaga aaccctaat tctaagaaaa acaaaaataa
4861 atatgcgcaa taccaaaagc aattagcagc acaagaacga aaaattactg aaacgaaaaa
```

FIG.16-6

```
4921 attgatagaa acagatggac ctgtattaga cttagctgca gttactata tctataccc
4981 tcatgaagtt tactacctat ccagtggttc aaaccctaaa tacaatgcct atatgggtgc
5041 gtacagactc caatgggaaa tgattcaatt tgcgaaaaat aaagtatta atcgctataa
5101 tttttacggt attacaggag atttcagtga agatgctgaa gattcggtg ttcaaaaatt
5161 caaagaaggc tttaatgccc atgttgaaga atatgtcggc gacttcatta aaccgattaa
5221 aaccttttat tataaaatc atcaattatt aaatagataa ctgaaaatta tttagtcttt
5281 gttaatcaaa tatgacacct caaaatgggt gtgaagagaa ctatattttc aaaggcgtta
5341 atctcgacat cagcgaaggt aaacgttcta gttttacatt cttaactact aagatgctat
5401 aatttggtta acgaagatta tatgcatatt aagcacctac ttccatcgaa aatatcgccg
5461 gaagataaga cgactatatt attataccat ctgtaaatat acaagcatat atacttctga
5521 taacagaacc ttgtagctga tgctggctat ggtagtaaaa gtaaggtttt gtttcaaagt
5581 aaaaatata gctaaccact aattatcat gtcagtgttc actcaacttg ctagcatgat
5641 gctaatttcg tggcatggcg aaaatccgta gatctgaaga gatctgcggt tctttttata
5701 tagaccgtaa atacattcaa taccttttaa agtattcttt gccgtattga tactttgata
5761 ccttgtcttt cttactttaa tatgacggtg gccttgctca ataaggttat tccgatattt
5821 cgatgtacaa tgacagtcat gtttaagttt aaaagcttta atgactttag ccatggctac
```

FIG.16-7

FROM FIG.16-6

```
5881 cttcgttgaa ggtgcctgat ctgtaattac cttttgaggt ttaccaaatt gttaatgag
5941 acgtttgata acgcatatg ctgaatgatt atctcgttgc ttacgcaagc aaatatctaa
6001 tgtatgggtt ctgtttttta taatacttta gaaaaccag cattatatgt atcactgata
6061 tttatattta tatttcatat aaatacttga acaaaaaatt catatttaat tttctttgtt
6121 gactaacaat atttatttat aagtatttgc tgtcattatt ctaatttatg gaggccgttt
6181 tttatgaact ttaaatatatt gtatgagaaa tttttcttgga tgagtcttgc ttggattta
6241 gtgtcatgca gtgtcttaag tggtattctg actcccttt gggaattcca ataggtatta
6301 ttttaggctt atatttggat ggattactaa aaaaggatgc ttcttgatat taacttaatt
6361 tttaataact ccagctaatt actgttaaag ttgtataatt attaaattaa ggaaacatta
6421 caagaaaagg aaatgcatat ttgtattcc tttcttgta atgttataaa aattaagatg
6481 ttataccta tctttattaa tgctataaac cgtctgcctt gtgatatc
```

FIG. 17

"MKKTKNNYYTRPLAIGLSTFALASIVYGGIQNETHASEKSNMDV

SKKVAEVETSKAPVENTAEVETSKAPVENTAEVETSKAPVE

NTAEVETSKAPVENTAEVETSKAPVENTAEVETSKAPVENTAEVET

SKAPVENTAEVETSKAPVENTAEVETSKAPVENTAEVETSKAPVE

NTAEVETSKAPVENTAEVETSKALVQNRTALRAATHEHSAQWLNNYKKGYGYGPYP

LGINGGMHYGVDFFMNIGTPVKAISSGKIVEAGWSNYGGGNQIGLIENDGVHRQWYMH

LSKYNVKVGDYVKAGQIIGWSGSTGYSTAPHLHFQRMVNSFSNSTAQDPMPFLKSAGYG

KAGGTVTPTPNTGWKTNKYGTLYKSESASFTPNTDIITRTTGPFRSMPQSGVLKAGQTIH

YDEVMKQDGHVWVGYTGNSGQRIYLPVRTWNKSTNTLGVLWGTIK"

SEQUENCE LISTING

<160> NUMBER OF SEQ ID NOS: 10

<210> SEQ ID NO 1
<211> LENGTH: 1486
<212> TYPE: DNA
<213> ORGANISM: Staphylococcus simulans

<400> SEQUENCE: 1

```
ccggaactct tgaatgttta gttttgaaaa ttccaaaaaa aaacctacct tcttaatatt      60
gattcatatt attttaacac aatcagttag aatttcaaaa atcttaaagt caatttttga     120
gtgtgtttgt atatttcatc aaaatcaatc aatattattt tactttcttc atcgttaaaa     180
aatgtaatat ttataaaaat atgctattct cataaatgta ataataaatt aggaggtatt     240
aaggttgaag aaaacaaaaa acaattatta tacgagacct ttagctattg gactgagtac     300
atttgcctta gcatctattg tttatggagg gattcaaaat gaaacacatg cttctgaaaa     360
aagtaatatg gatgtttcaa aaaagtagc tgaagtagag acttcaaaag ccccagtaga     420
aaatacagct gaagtagaga cttcaaaagc tccagtagaa aatacagctg aagtagagac     480
ttcaaaagct ccagtagaaa atacagctga agtagagact tcaaaagctc cagtagaaaa     540
tacagctgaa gtagagactt caaaagctcc ggtagaaaat acagctgaag tagagacttc     600
aaaagcccca gtagaaaata cagctgaagt agagacttca aaagccctgg ttcaaaatag     660
aacagcttta agagctgcaa cacatgaaca ttcagcacaa tggttgaata attacaaaaa     720
aggatatggt tacggtcctt atccattagg tataaatggc ggtatgcact acggagttga     780 ttttttatg aatattggaa caccagtaaa agctatttca agcggaaaaa tagttgaagc     840
tggttggagt aattacggag gaggtaatca aataggtctt attgaaaatg atggagtgca     900
tagacaatgg tatatgcatc taagtaaata gtaggagatt gtaggagatt atgtcaaagc     960
tggtcaaata atcggttggt ctggaagcac tggttattct acagcaccac atttacactt    1020
```

-continued

```
ccaaagaatg gttaattcat tttcaaattc aactgcccaa gatccaatgc ctttcttaaa    1080
gagcgcagga tatggaaaag caggtggtac agtaactcca cgccgaata caggttggaa    1140 aacaaacaaa tatggcacac tatataaatc agagtcagct agcttcacac ctaatacaga    1200
tataataaca agaacgactg gtccatttag aagcatgccg cagtcaggag tcttaaaagc    1260
aggtcaaaca attcattatg atgaagtgat gaaacaagac ggtcatgttt gggtaggtta    1320
tacaggtaac agtggccaac gtatttactt gcctgtaaga acatggaata aatctactaa    1380
tactttaggt gttctttggg gaactataaa gtgagcgcgc tttttataaa cttatatgat    1440
aattagagca aataaaaatt ttttctcatt cctaaagttg aagctt                   1486
```

<210> SEQ ID NO 2
<211> LENGTH: 388
<212> TYPE: PRT
<213> ORGANISM: Staphylocccus simulans

<400> SEQUENCE: 2

```
Met Lys Lys Thr Lys Asn Asn Tyr Tyr Thr Arg Pro Leu Ala Ile Gly
  1               5                  10                  15

Leu Ser Thr Phe Ala Leu Ala Ser Ile Val Tyr Gly Gly Ile Gln Asn
             20                  25                  30

Glu Thr His Ala Ser Glu Lys Ser Asn Met Asp Val Ser Lys Lys Val
         35                  40                  45

Ala Glu Val Glu Thr Ser Lys Ala Pro Val Glu Asn Thr Ala Glu Val
     50                  55                  60

Glu Thr Ser Lys Ala Pro Val Glu Asn Thr Ala Glu Val Glu Thr Ser
 65                  70                  75                  80

Lys Ala Pro Val Glu Asn Thr Ala Glu Val Glu Thr Ser Lys Ala Pro
                 85                  90                  95

Val Glu Asn Thr Ala Glu Val Glu Thr Ser Lys Ala Pro Val Glu Asn
            100                 105                 110

Thr Ala Glu Val Glu Thr Ser Lys Ala Pro Val Glu Asn Thr Ala Glu
        115                 120                 125

Val Glu Thr Ser Lys Ala Leu Val Gln Asn Arg Thr Ala Leu Arg Ala
    130                 135                 140

Ala Thr His Glu His Ser Gln Trp Leu Asn Asn Tyr Lys Lys Gly Tyr
145                 150                 155                 160

Gly Tyr Gly Pro Tyr Pro Leu Gly Ile Asn Gly Gly Met His Tyr Gly
                165                 170                 175

Val Asp Glu Phe Met Asn Ile Gly Thr Pro Val Lys Ala Ile Ser Ser
            180                 185                 190

Gly Lys Ile Val Glu Ala Gly Trp Ser Asn Tyr Gly Gly Gly Asn Gln
        195                 200                 205

Ile Gly Leu Ile Glu Asn Asp Gly Val His Arg Gln Glu Tyr Met His
    210                 215                 220

Leu Ser Lys Tyr Asn Val Lys Val Gly Asp Tyr Val Lys Ala Gly Gln
225                 230                 235                 240

Ile Ile Gly Trp Ser Gly Ser Thr Gly Tyr Ser Thr Ala Pro His Leu
                245                 250                 255

His Phe Gln Arg Met Val Asn Ser Phe Ser Asn Ser Thr Ala Gln Asp
            260                 265                 270

Pro Met Pro Phe Leu Lys Ala Ser Gly Tyr Gly Lys Ala Gly Gly Thr
        275                 280                 285

Val Thr Pro Thr Pro Asn Thr Gly Trp Lys Thr Asn Lys Tyr Gly Thr
```

```
                290             295             300
Leu Tyr Lys Ser Glu Ser Ala Ser Phe Thr Pro Asn Thr Asp Ile Ile
305                 310                 315                 320

Thr Arg Thr Thr Gly Pro Phe Arg Ser Met Pro Gln Ser Gly Val Leu
                325                 330                 335

Lys Ala Gly Gln Thr Ile His Tyr Asp Glu Val Met Lys Gln Asp Gly
            340                 345                 350

His Val Trp Val Gly Tyr Thr Gly Asn Ser Gly Gln Arg Ile Tyr Leu
        355                 360                 365

Pro Val Arg Thr Trp Asn Lys Ser Thr Asn Thr Leu Gly Val Leu Trp
    370                 375                 380

Gly Thr Ile Lys
385

<210> SEQ ID NO 3
<211> LENGTH: 741
<212> TYPE: DNA
<213> ORGANISM: Staphylococcus simulans

<400> SEQUENCE: 3
gccgcaacac atgaacattc agcacaatgg ttgaataatt acaaaaaagg atatggttac    60
ggcccttatc cattaggtat aaatggcggt atgcactacg gagttgattt ttttatgaat   120
attggaacac cagtaaaagc tatttcaagc ggaaaaatag ttgaagctgg ttggagtaat   180
tacggaggag gtaatcaaat aggtcttatt gaaaatgatg gagtgcatag acaatggtat   240
atgcatctaa gtaaatataa tgttaaagta ggagattatg tcaaagctgg tcaaataatc   300
ggttggtctg gaagcactgg ttattctaca gcaccacatt tacacttcca agaatggtt    360
aactcatttt cacagtcaac tgcccaagat ccaatgcctt tcttaaagag cgcaggatat   420
ggaaaagcag gtggtacagt aactccaacg ccgaatacag gttggaaaac aaacaaatat   480
ggcacactat ataaatcaga gtcagctagc ttcacaccta atacagatat aataacaaga   540
acgactggtc catttagaag catgccgcag tcaggagtct taaaagcagg tcaaacaatt   600
cattatgatg aagtgatgaa acaagacggt catgtttggg taggttatac aggtaacagt   660
ggccaacgta tttacttgcc tgtgagaaca tggcagaagt ctactaatac tctgggtgtt   720
ctgtggggaa ctataaagtg a                                              741

<210> SEQ ID NO 4
<211> LENGTH: 1520
<212> TYPE: DNA
<213> ORGANISM: Staphylococcus simulans

<400> SEQUENCE: 4
tgtgtgcgtg ctcccattcg ttcatgctcg ccacgcgcac ggccgcgctt tgcgacgcga    60
tcgcgcaccg tgtgaaccgc attgaggaat ggccgttcgg caagcgcatg tacggcctcg   120
atttgaacgt gcgtcgcacg acagcgtcgc cccgcggtc agagtccggc gcccgcggta   180
tacgacagc gatcgcggcg tccgccgatg acgaacggtc gtgcgcgtca gtcgcatgcg   240
ccgctcgccg ctggcgttcc ggcttcgcgg gcgcagcgcg gtccaccact cttcaaacgt   300
cttcctcggg agcagcatat gaagaagatt ccaaggcgg gactgggct ggcgctggtg    360
tgcgcgctgg cgacgatcgg cggcaacgca gcgcgcaggg ccacggctca gcggcgagga   420
tctggtgtat tctacgacga gatgttcgac ttcgacatcg atgcgcatct ggccaagcat   480
gcgccgcatc tgcacaagca ctcggaagag atctcgcact gggccggcta cagcgggatc   540
```

-continued

```
agccgaagtg ttgatcgcgc tgatggagca gcagagcgcg cggtcacgcc aagcgcgcga      600
cgaatcgtcc gttcggcaag ctggcgcgcg ccgacggctt cggcgcgcag acccgcgagg      660
tcgcgctggc gctgcgcgag tcgctgtacg agcgcgatcc cgacgcgcca aggggccggt      720
gacgctggcc cgcgccaatc cgctgcaggc gctgttcgag cgttccggcg acaacgagcc      780
ggcggccgcg ctgcgcggcg acggcgagtt ccagctggtc tacggccgcc tgttcaacga      840
accgcgccag gccaaggcgg cttcggaccg cttcgccaag gccggcccgg acgtgcagcc      900
gtgtcgccca acggcctgct gcagttcccc ttcccgcgcg cgccagctg gcatgtcggc       960 ggcgcccaca ccaacaccgg ctcgggcaat tacccgatgt cgtcgctgga catgtcgcgc     1020
ggcggcggct ggggcagcaa ccagaacggc aactgggtgt cggcctcggc cgccggctcg     1080
ttcaagcgcc actcttcgtg cttcgcggag atcgtgcaca ccggcggctg gtcgacgacc     1140
tactaccacc tgatgaacat ccagtacaac accggcgcca acgtgtcgat gaacaccgcc     1200
atcgccaacc cggccaacac ccaggcgcag gcgctgtgca acggcggcca gtcgaccggc     1260
ccgcacgagc attggtcgtt gaagcagaac ggcagcttct accacctcaa cggcacctac     1320
ctgtcgggct atcgcatcac cgcgaccggc agcagctatg acaccaactg cagccggttc     1380
tatctgacca agaacggcca gaactactgc tacggctatt acgtcaaccc gggcccgaac     1440
tgaggctcgc cgcgtgcgtt gcccgcgtcc tcaagcgccc cacgcgcggg gcgcgggcac     1500
cggccgggtc aggtcgaatt                                                  1520
```

<210> SEQ ID NO 5
<211> LENGTH: 480
<212> TYPE: PRT
<213> ORGANISM: Staphylococcus simulans

<400> SEQUENCE: 5

```
Met Lys Lys Thr Lys Asn Asn Tyr Tyr Thr Thr Pro Leu Ala Ile Gly
  1               5                  10                  15

Leu Ser Thr Phe Ala Leu Ala Ser Ile Val Tyr Gly Gly Ile Gln Asn
             20                  25                  30

Glu Thr His Ala Ser Glu Lys Ser Asn Met Asp Val Ser Lys Lys Val
         35                  40                  45

Ala Glu Val Glu Thr Ser Lys Pro Pro Val Glu Asn Thr Ala Glu Val
     50                  55                  60

Glu Thr Ser Lys Ala Pro Val Glu Asn Thr Ala Glu Val Glu Thr Ser
 65                  70                  75                  80

Lys Ala Pro Val Glu Asn Thr Ala Glu Val Glu Thr Ser Lys Ala Pro
                 85                  90                  95

Val Glu Asn Thr Ala Glu Val Glu Thr Ser Lys Ala Pro Val Glu Asn
            100                 105                 110

Thr Ala Glu Val Glu Thr Ser Lys Ala Pro Val Glu Asn Thr Ala Glu
        115                 120                 125

Val Glu Thr Ser Lys Ala Pro Val Glu Asn Thr Ala Glu Val Glu Thr
    130                 135                 140

Ser Lys Ala Pro Val Glu Asn Thr Ala Glu Val Glu Thr Ser Lys Ala
145                 150                 155                 160

Pro Val Glu Asn Thr Ala Glu Val Glu Thr Ser Lys Ala Pro Val Glu
                165                 170                 175

Asn Thr Ala Glu Val Glu Thr Ser Lys Ala Pro Val Glu Asn Thr Ala
            180                 185                 190
```

```
Glu Val Glu Thr Ser Lys Ala Pro Val Glu Asn Thr Ala Glu Val Glu
            195                 200                 205

Thr Ser Lys Ala Pro Val Glu Asn Thr Ala Glu Val Glu Thr Ser Lys
210                 215                 220

Ala Leu Val Gln Asn Arg Thr Ala Leu Arg Ala Thr His Glu His
225                 230                 235                 240

Ser Ala Gln Trp Leu Asn Asn Tyr Lys Tyr Gly Tyr Gly Tyr Gly Pro
            245                 250                 255

Tyr Pro Leu Gly Ile Asn Gly Gly Ile His Tyr Gly Val Asp Phe Phe
            260                 265                 270

Met Asn Ile Gly Thr Pro Val Lys Ala Ile Ser Ser Gly Lys Ile Val
            275                 280                 285

Glu Ala Gly Trp Ser Asn Tyr Gly Gly Gly Asn Gln Ile Gly Leu Ile
290                 295                 300

Glu Asn Asp Gly Val His Arg Gln Trp Tyr Met His Leu Ser Lys Tyr
305                 310                 315                 320

Asn Val Lys Val Gly Asp Tyr Val Lys Ala Gly Gln Ile Ile Gly Trp
            325                 330                 335

Ser Gly Ser Thr Gly Tyr Ser Thr Ala Pro His Leu His Phe Gln Arg
            340                 345                 350

Met Val Asn Ser Phe Ser Asn Ser Thr Ala Gln Asp Pro Met Pro Phe
            355                 360                 365

Leu Lys Ser Ala Gly Tyr Gly Lys Ala Gly Gly Thr Val Thr Pro Thr
            370                 375                 380

Pro Asn Thr Gly Trp Lys Thr Asn Lys Tyr Gly Thr Leu Tyr Lys Ser
385                 390                 395                 400

Glu Ser Ala Ser Phe Thr Pro Asn Thr Asp Ile Ile Thr Arg Thr Thr
                405                 410                 415

Gly Pro Phe Arg Ser Met Pro Gln Ser Gly Val Leu Lys Ala Gly Gln
            420                 425                 430

Thr Ile His Tyr Asp Glu Val Met Lys Gln Asp Gly His Val Trp Val
            435                 440                 445

Gly Tyr Thr Gly Asn Ser Gly Gln Arg Ile Tyr Leu Pro Val Arg Thr
            450                 455                 460

Trp Asn Lys Ser Thr Asn Thr Leu Gly Val Leu Trp Gly Thr Ile Lys
465                 470                 475                 480

<210> SEQ ID NO 6
<211> LENGTH: 492
<212> TYPE: PRT
<213> ORGANISM: Achromobacter lyticus

<400> SEQUENCE: 6

Met Lys Lys Thr Lys Asn Asn Tyr Tyr Thr Arg Pro Leu Ala Ile Gly
1               5                   10                  15

Leu Ser Thr Phe Ala Leu Ala Ser Ile Val Tyr Gly Gly Ile Gln Asn
            20                  25                  30

Glu Thr His Ala Ser Glu Lys Ser Asn Met Asp Val Ser Lys Lys Val
        35                  40                  45

Ala Glu Val Glu Thr Ser Lys Ala Pro Val Glu Asn Thr Ala Glu Val
    50                  55                  60

Glu Thr Ser Lys Ala Pro Val Glu Asn Thr Ala Glu Val Glu Thr Ser
65                  70                  75                  80

Lys Ala Pro Val Glu Asn Thr Ala Glu Val Glu Thr Ser Lys Ala Pro
                85                  90                  95
```

-continued

Val Glu Asn Thr Ala Glu Val Glu Thr Ser Lys Ala Pro Val Glu Asn
                100                 105                 110

Thr Ala Glu Val Glu Thr Ser Lys Ala Pro Val Glu Asn Thr Ala Glu
            115                 120                 125

Val Glu Thr Ser Lys Ala Pro Val Glu Asn Thr Ala Glu Val Glu Thr
        130                 135                 140

Ser Lys Ala Pro Val Glu Asn Thr Ala Glu Val Glu Thr Ser Lys Ala
145                 150                 155                 160

Pro Val Glu Asn Thr Ala Glu Val Glu Thr Ser Lys Ala Pro Val Glu
                165                 170                 175

Asn Thr Ala Glu Val Glu Thr Ser Lys Ala Pro Val Glu Asn Thr Ala
            180                 185                 190

Glu Val Glu Thr Ser Lys Ala Pro Val Glu Asn Thr Ala Glu Val Glu
        195                 200                 205

Thr Ser Lys Ala Pro Val Glu Asn Thr Ala Glu Val Glu Thr Ser Lys
210                 215                 220

Ala Pro Val Glu Asn Thr Ala Glu Val Glu Thr Ser Lys Ala Leu Val
225                 230                 235                 240

Gln Arg Thr Ala Leu Arg Ala Ala Thr His Glu His Ser Ala Gln Trp
                245                 250                 255

Leu Asn Asn Tyr Lys Lys Gly Tyr Gly Tyr Gly Pro Tyr Pro Leu Gly
            260                 265                 270

Ile Asn Gly Gly Met His Tyr Gly Val Asp Phe Phe Met Asn Ile Gly
        275                 280                 285

Thr Pro Val Lys Ala Ile Ser Ser Gly Lys Ile Val Glu Ala Gly Trp
        290                 295                 300

Ser Asn Tyr Gly Gly Gly Asn Gln Ile Gly Leu Ile Glu Asn Asp Gly
305                 310                 315                 320

Val His Arg Gln Trp Tyr Met His Leu Ser Lys Tyr Asn Val Lys Val
                325                 330                 335

Gly Asp Tyr Val Lys Ala Gly Gln Ile Ile Gly Trp Ser Gly Ser Thr
            340                 345                 350

Gly Tyr Ser Thr Ala Pro His Leu His Phe Gln Arg Met Val Asn Ser
        355                 360                 365

Phe Ser Asn Ser Thr Ala Gln Asp Pro Met Pro Phe Leu Lys Ser Ala
370                 375                 380

Gly Tyr Gly Lys Ala Gly Gly Thr Val Thr Pro Thr Asn Thr Gly
385                 390                 395                 400

Trp Lys Thr Asn Lys Tyr Gly Thr Leu Tyr Lys Ser Glu Ser Ala Ser
                405                 410                 415

Phe Thr Pro Asn Thr Asp Ile Ile Thr Arg Thr Thr Gly Pro Phe Arg
            420                 425                 430

Ser Met Pro Gln Ser Gly Val Leu Lys Ala Gly Gln Thr Ile His Tyr
        435                 440                 445

Asp Glu Val Met Lys Gln Asp Gly His Val Trp Val Gly Tyr Thr Gly
450                 455                 460

Asn Ser Gly Gln Arg Ile Tyr Leu Pro Val Arg Thr Trp Asn Lys Ser
465                 470                 475                 480

Thr Asn Thr Leu Gly Val Leu Trp Gly Thr Ile Lys
            485                 490

<210> SEQ ID NO 7
<211> LENGTH: 741

```
<212> TYPE: DNA
<213> ORGANISM: Artificial Sequence
<220> FEATURE:
<223> OTHER INFORMATION: Description of Artificial Sequence: altered S.
      simulans lysostaphin gene

<400> SEQUENCE: 7
gctgcaacac atgaacattc agcacaatgg ttgaataatt acaaaaaagg atatggttac      60
ggtccttatc cattaggtat aaatggcggt atgcactacg gagttgattt ttttatgaat     120
attggaacac cagtaaaagc tatttcaagc ggaaaaatag ttgaagctgg ttggagtaat     180
tacggaggag gtaatcaaat aggtcttatt gaaaatgatg gagtgcatag acaatggtat     240
atgcatctaa gtaaatataa tgttaaagta ggagattatg tcaaagctgg tcaaataatc     300
ggttggtctg gaagcactgg ttattctaca gcaccacatt tacacttcca agaatggtt     360
aattcatttt caaattcaac tgcccaagat ccaatgcctt tcttaaagag cgcaggatat     420
ggaaaagcag gtggtacagt aactccaacg ccgaatacag gttggaaaac aaacaaatat     480
ggcacactat ataaatcaga gtcagctagc ttcacaccta atacagatat aataacaaga     540
acgactggtc catttagaag catgccgcag tcaggagtct taaaagcagg tcaaacaatt     600
cattatgatg aagtgatgaa acaagacggt catgtttggg taggttatac aggtaacagt     660
ggccaacgta tttacttgcc tgtaagaaca tggaataaat ctactaatac tttaggtgtt     720
ctttggggaa ctataaagtg a                                              741

<210> SEQ ID NO 8
<211> LENGTH: 480
<212> TYPE: PRT
<213> ORGANISM: Staphylococcus simulans

<400> SEQUENCE: 8
```

Met Lys Lys Thr Lys Asn Asn Tyr Tyr Thr Thr Pro Leu Ala Ile Gly
 1               5                  10                  15

Leu Ser Thr Phe Ala Leu Ala Ser Ile Val Tyr Gly Gly Ile Gln Asn
            20                  25                  30

Glu Thr His Ala Ser Glu Lys Ser Asn Met Asp Val Ser Lys Lys Val
        35                  40                  45

Ala Glu Val Glu Thr Ser Lys Pro Pro Val Glu Asn Thr Ala Glu Val
    50                  55                  60

Glu Thr Ser Lys Ala Pro Val Glu Asn Thr Ala Glu Val Glu Thr Ser
65                  70                  75                  80

Lys Ala Pro Val Glu Asn Thr Ala Glu Val Glu Thr Ser Lys Ala Pro
                85                  90                  95

Val Glu Asn Thr Ala Glu Val Glu Thr Ser Lys Ala Pro Val Glu Asn
            100                 105                 110

Thr Ala Glu Val Glu Thr Ser Lys Ala Pro Val Glu Asn Thr Ala Glu
        115                 120                 125

Val Glu Thr Ser Lys Ala Pro Val Glu Asn Thr Ala Glu Val Glu Thr
    130                 135                 140

Ser Lys Ala Pro Val Glu Asn Thr Ala Glu Val Glu Thr Ser Lys Ala
145                 150                 155                 160

Pro Val Glu Asn Thr Ala Glu Val Glu Thr Ser Lys Ala Pro Val Glu
                165                 170                 175

Asn Thr Ala Glu Val Glu Thr Ser Lys Ala Pro Val Glu Asn Thr Ala
            180                 185                 190

Glu Val Glu Thr Ser Lys Ala Pro Val Glu Asn Thr Ala Glu Val Glu

-continued

```
                    195                 200                 205
Thr Ser Lys Ala Pro Val Glu Asn Thr Ala Glu Val Glu Thr Ser Lys
        210                 215                 220

Ala Leu Val Gln Asn Arg Thr Ala Leu Arg Ala Ala Thr His Glu His
225                 230                 235                 240

Ser Ala Gln Trp Leu Asn Asn Tyr Lys Tyr Gly Tyr Gly Tyr Gly Pro
            245                 250                 255

Tyr Pro Leu Gly Ile Asn Gly Gly Ile His Tyr Gly Val Asp Phe Phe
            260                 265                 270

Met Asn Ile Gly Thr Pro Val Lys Ala Ile Ser Ser Gly Lys Ile Val
        275                 280                 285

Glu Ala Gly Trp Ser Asn Tyr Gly Gly Asn Gln Ile Gly Leu Ile
        290                 295                 300

Glu Asn Asp Gly Val His Arg Gln Trp Tyr Met His Leu Ser Lys Tyr
305                 310                 315                 320

Asn Val Lys Val Gly Asp Tyr Val Lys Ala Gly Gln Ile Ile Gly Trp
                325                 330                 335

Ser Gly Ser Thr Gly Tyr Ser Thr Ala Pro His Leu His Phe Gln Arg
            340                 345                 350

Met Val Asn Ser Phe Ser Asn Ser Thr Ala Gln Asp Pro Met Pro Phe
            355                 360                 365

Leu Lys Ser Ala Gly Tyr Gly Lys Ala Gly Gly Thr Val Thr Pro Thr
        370                 375                 380

Pro Asn Thr Gly Trp Lys Thr Asn Lys Tyr Gly Thr Leu Tyr Lys Ser
385                 390                 395                 400

Glu Ser Ala Ser Phe Thr Pro Asn Thr Asp Ile Ile Thr Arg Thr Thr
                405                 410                 415

Gly Pro Phe Arg Ser Met Pro Gln Ser Gly Val Leu Lys Ala Gly Gln
            420                 425                 430

Thr Ile His Tyr Asp Glu Val Met Lys Gln Asp Gly His Val Trp Val
        435                 440                 445

Gly Tyr Thr Gly Asn Ser Gly Gln Arg Ile Tyr Leu Pro Val Arg Thr
450                 455                 460

Trp Asn Lys Ser Thr Asn Thr Leu Gly Val Leu Trp Gly Thr Ile Lys
465                 470                 475                 480
```

<210> SEQ ID NO 9
<211> LENGTH: 1825
<212> TYPE: DNA
<213> ORGANISM: Staphylococcus simulans

<400> SEQUENCE: 9

```
gaaaattcca aaaaaaaacc tactttctta atattgattc atattatttt aacacaatca    60
gttagaattt caaaatctt aaagtcaatt tttgagtgtg tttgtatatt tcatcaaagc    120
caatcaatat tattttactt tcttcatcgt taaaaaatgt aatatttata aaaatatgct    180
attctcataa atgtaataat aaattaggag gtattaaggt tgaagaaaac aaaaaacaat    240
tattatacga caccctttagc tattggactg agtacatttg ccttagcatc tattgtttat    300
ggagggattc aaaatgaaac acatgcttct gaaaaaagta atatggatgt ttcaaaaaaa    360
gtagctgaag tagagacttc aaaacccccca gtagaaaata cagctgaagt agagacttca    420
aaagctccag tagaaaatac agctgaagta gagacttcaa aagctccagt agaaaataca    480
gctgaagtag agacttcaaa agctccagta gaaaatacag ctgaagtaga gacttcaaaa    540
```

-continued

```
gctccggtag aaaatacagc tgaagtagag acttcaaaag ctccggtaga aaatacagct      600
gaagtagaga cttcaaaagc cccagtagaa aatacagctg aagtagagac ttcaaaagct      660
ccagtagaaa atacagctga agtagagact caaaagctc cggtagaaaa tacagctgaa       720
gtagagactt caaaagcccc agtagaaaat acagctgaag tagagacttc aaaagctcca      780
gtagaaaata cagctgaagt agagacttca aaagctccgg tagaaaatac agctgaagta      840
gagacttcaa aagccccagt agaaaataca gctgaagtag agacttcaaa agccctggtt      900
caaaatagaa cagctttaag agctgcaaca catgaacatt cagcacaatg gttgaataat      960
tacaaaaaag gatatggtta cggtccttat ccattaggta taaatggcgg tatccactac     1020
ggagttgatt ttttatgaa tattggaaca ccagtaaaag ctatttcaag cggaaaaata     1080
gttgaagctg ttggagtaa ttacggagga ggtaatcaaa taggtcttat tgaaaatgat      1140
ggagtgcata gacaatggta tatgcatcta agtaaatata atgttaaagt aggagattat     1200
gtcaaagctg tcaaataat cggttggtct ggaagcactg ttattctac agcaccacat      1260 ttacacttcc aaagaatggt taattcattt tcaaattcaa ctgcccaaga tccaatgcct     1320
ttcttaaaga gcgcaggata tggaaaagca ggtggtacag taactccaac gcccaataca     1380
ggttggaaaa caaacaaata tggcacacta tataaatcag agtcagctag cttcacacct     1440
aatacagata taataacaag aacgactggt ccatttagaa gcatgccgca gtcaggagtc     1500
ttaaaagcag gtcaaacaat tcattatgat gaagtgatga acaagacgg tcatgtttgg      1560 gtaggttata caggtaacag tggccaacgt atttacttgc ctgtaagaac atggaataaa     1620
tctactaata ctttaggtgt tctttgggga actataaagt gagcgcgctt tttataaact     1680
tatatgataa ttagagcaaa taaaaatttt ttctcattcc taaagttgaa gcttttcgta     1740
atcatgtcat agcgtttcct gtgtgaaatt gcttagcctc acaattccac acaacatacg     1800
agccggaaca taaagtgcta agcct                                           1825
```

<210> SEQ ID NO 10
<211> LENGTH: 6457
<212> TYPE: DNA
<213> ORGANISM: Achromobacter lyticus

<400> SEQUENCE: 10

```
gatatcattt caaagacaga tattctaaag aaaagatata ttttaaaaaa tgtggttgaa       60
aaaattaaag aaattcacga ttttgactat atatttattg atgtaccacc tactattaac      120
tctgatttca ctaataatgc tgtttacgca agtgattaca ttttaatggt atttcaaaca      180
caacaatctg cttatgaaag tagtctttca tttgttaatt ttttaaggga tcgaaaaaaa      240
gaatcagatt tatcatttga attggttggc gctgttccag tattaattaa aaaaagtgga      300
cgtgtagata acagatatt agatatgtct aaatcagcat tttctgaagc actctttgag       360
aaccagatat atcaaagaga aagaataaaa aaatttgccg ctgatggaat aaaagataaa      420
gatatgcatg acaaaaaagt tatatatatg tttaacaaag tctacgaaga attagttgat      480
agagttagat taattgaagg tgagtgatat ttatggcagg atttttagat aacatagata      540
catctgaggt aaaatatacg gaaaattata aaccggtatc taaaagtacg actatgagag      600
tggacactga tataaaaaaa agattaaatc aaatggcgtt agataaagat acatctataa      660
aggctatagt tgatgaagtg ttaggagaat ttttgaaaaa aaataagtat tagtatttta      720
tataggctct atactattta ggactggtga taatcactag tcctattttt gatacaaaaa      780
agcgcaatta tctctataat tagaagtatc ctaccaccaa taattaagga ataatgcgc       840
```

-continued

```
ctatgtctaa tattatatca atcacccttg gaattaaaga taaaaatatc acttttgaag      900
ataaggttga agaaagtata aagggaaaaa ttctttattt tactttggaa aattaataca      960
ttctcccaag cgatgtaaac tttgcggaca cgaaaatacg aacttttcta taatcaaaaa     1020
tggttttaaa aaatcatgtc ttacgatacc taaggtatcg gagaagccag cttatttaat     1080
attggaaaaa cagcgtttcc actgtaaaaa gtgctgcagt tatttcactg ctgaaacacc     1140
tgtcgttgag tggaattgct atatttctca aaacacacga ttagctgtgc tgaataagtc     1200
gatagacata cgttcgcaaa aatctgttgc tgaatcttgt catgtcagta attccacagt     1260
tactcgaata attaataaag ctgcttctca aatagctcaa acaccgttta aatatttacc     1320
ggaacacttg atgatggatg agttcaaaag cgttaaaaat gttgtcggta aaatgagttt     1380
tatttatgca gatgcagtaa cacaccgtat tattgatatt gtgcctgacc gcaggttatt     1440
tgctttgaaa aattatttct accgttatcc tctttctgaa agaaaatgtg tgaaagcagt     1500
gtctattgat atgtatgaac cttatatggc tttgatcaga gaagttttc ctaatgccaa      1560
aattctaata gttcatttcc atattgttca gtctttaaat aaagccttga acatgactcg     1620
agtaacagtt atgaatagtt tcagaacaac tgaaagacct ctatacaaca agtacaagcg     1680
ttactggaag attcttttaa aactgccttg aaaaatatag aaatcaatag cgttgctcct     1740
aaacttcaaa cagctgttaa aacactaaga aagcacaata gaatgataag aaatactttt     1800
gaatacagta acttgaccaa cggttcactt gagggaataa atactaaaat aaagctgata     1860
cagagaatat cttttggtta tagaaatttt ggtgatttac gcagtcgtat cattttatgt     1920
acaaatcttt ttgcagctaa tccaaaaaaa gagatcaagc aactttatgc tgcttaatct     1980
ctgcgtttta gctcaccagt cttatttgac agagagccaa taaattaac ggagggagaa      2040
ggattcgaac caacgcaagc acatacatgc tcctaattaa taaaaatata ttaatcccct     2100
taatccagac ttgggtatcc ctccacaagc attatttaat gctaatataa catatataac     2160
aacaaatgtc aatatgtatt tataaggaaa aggatattaa aattattctg agttatataa     2220
ggtagtattc ataatcatcc taagttgaa gtcgaaaagc ttcaacttta ggaatgagaa      2280
aaaattttta tttgctctaa ttatcatata agtttataaa aagcgcgctc actttatagt     2340
tccccaaaga acacctaaag tattagtaga tttattccat gttcttacag gcaagtaaat     2400
acgttggcca ctgttacctg tataacctac ccaaacatga ccgtcttgtt tcatcacttc     2460
atcataatga attgtttgac ctgcttttaa gactcctgac tgcggcatgc ttctaaatgg     2520
tagtgtgcca cttgttatta tatctgtatt aggtgtgaag ctagctgact ctgatttata     2580
accagtcgtt tatttgtttg ttttccaacc tgtattcggc gttggagtta ctgtaccacc     2640
tgcttttcca tatcctgcgc tctttaagaa aggcattgga tcttgggcag ttgaatttga     2700
aaatgaatta accattcttt ggaagtgtaa atgtggtgct gtagaataac cagtgcttcc     2760
agaccaaccg attatttgac cagctttgac ataatctcct actttaacat tatatttact     2820
tagatgcata taccattgtc tatgcactcc atcattttca ataagaccta tttgattacc     2880
tcctccgtaa ttactccaac cagcttcaac tattttccg cttgaaatag cttttactgg      2940
tgttccaata ttcataaaaa aatcaactcc gtagtgcata ccgccattta tacctaatgg     3000
ataaggaccg taaccatatc cttttttgta attattcaac cattgtgctg aatgttcatg     3060
tgttgcagct cttaaagctg ttctattttg aaccagggct tttgaagtct ctacttcagc     3120
tgtatttttct actggggctt ttgaagtctc tacttcagct gtattttcta ccggagcttt     3180
```

-continued

```
tgaagtctct acttcagctg tattttctac tggagctttt gaagtctcta cttcagctgt   3240
attttctact ggggcttttg aagtctctac ttcagctgta ttttctaccg gagcttttga   3300
agtctctact tcagctgtat tttctactgg agcttttgaa gtctctactt cagctgtatt   3360
ttctactggg gcttttgaag tctctacttc agctgtattt tctaccggag cttttgaagt   3420
taccggagct tttgaagtct ctacttcagt gtattttcta ctggagcttt tgaagtctct   3480
acttcagctg tattttctac tggagctttt gaagtctcta cttcagctgt attttctact   3540
ggagcttttg aagtctctac ttcagctgta ttttctactg ggcttttga agtctctact    3600
tcagctactt ttttgaaac atccatatta cttttttcag aagcatgtgt tcattttga    3660
atccctccat aaacaataga tgctaaggca aatgtactca gtccaatagc taaaggtctc   3720
gtataataat tgttttttgt tttcttcaac cttaatacct cctaatttat tattacatttt  3780
atgagaatag catatttta taaatattac attttttaac gatgaagaaa gtaaaataat   3840
attgattgat tttgatgaaa tatacaaaca cactcaaaaa ttgactttaa gattttttgaa 3900
attctaactg attgtgttaa aataatatga atcaatatta agaaagtagg ttttttttg    3960
gaattttcaa aactaaacat tcaagagttc gaagaatttg tgtttcaaaa aatgtctcat   4020
tacacacaat ctgcttctca ttttgaatat agaaataacc atcagaataa tgtgcattta   4080
gttggcgtaa aaaatgaaac aggtgaagta ttagctgctt gtttactgac tgaggcacgt   4140
tgtttaaagt tctttaaata tttctataca catcgcggtc cagtcatgaa ctttaaagac   4200
catgagttag tcagattttt ttatgaaaac ttaacgacct atctaaaaaa gcaaaactgc   4260
ttatatgttt taactgaccc ttacctgtta gaaaatattc gaagttgtga cggagaaatc   4320
cttgaatctt atgataacga aacttttatg aacgtgatga attttattagg ttaccgtcat   4380
caagggttta ctacaggtta ttctcaaaca agtcagatca gatggttgtc ggtcttaaac   4440
ctagaaaata aagatgaaaa acaattgtta aaagaaatgg attatcaaac acgccgtaat   4500
attaagaaaa cctatgaaat gcaggtgaaa gtccgcgatt tatcaattaa tgaaacagat   4560
cgatttttta aattatttaa aatggctgaa gaaaaacatg gcttcaaata agttattttg   4620
aaagaatgca gaaaacatac gctgataata gtatgttaaa gctggcttac atcgatttag   4680
aagaattatt agagacacaa aatgcgaaag tcgctgagtt aaatacagat attgaaaata   4740
ttcaagcggc attaaaagaa aaccctaatt ctaagaaaaa caaaaataaa tatgcgcaat   4800
accaaaagca attagcagca caagaacgaa aaattactga aacgaaaaaa ttgatagaaa   4860
cagatggacc tgtattagac ttagctgcag cttactatat ctatacccct catgaagttt   4920
actacctatc cagtggttca aaccctaaat acaatgccta tatgggtgcg tacagactcc   4980
aatgggaaat gattcaattt gcgaaaaata aggtattaa tcgctataat ttttacggta    5040
ttacaggaga tttcagtgaa gatgctgaag atttcggtgt tcaaaaattc aaagaaggct   5100
ttaatgccca tgttgaagaa tatgtcggcg acttcattaa accgattaaa cctttattt    5160
ataaaattca tcaattatta aatagataac tgaaaattat ttagtctttg ttaatcaaat   5220
atgacacctc aaaatgggtg tgaagagaac tatattttca aaggcgttaa tctcgacatc   5280
agcgaaggta aacgttctag ttttacattc ttaactacta agatgctata atttggttaa   5340
cgaagattat atgcatatta agcacctact tccatcgaaa atatcgccgg aagataagac   5400
gactatatta ttataccatc tgtaaatata caagcatata tacttctgat aacagaacct   5460
tgtagctgat gctggctatg gtagtaaaag taaggttttg tttcaaagta aaaaatatag   5520
ctaaccacta atttatcatg tcagtgttca ctcaacttgc tagcatgatg ctaatttcgt   5580
```

```
ggcatggcga aaatccgtag atctgaagag atctgcggtt cttttttatat agaccgtaaa    5640 tacattcaat accttttaaa gtattctttg ccgtattgat actttgatac cttgtctttc    5700
ttactttaat atgacggtgg ccttgctcaa taaggttatt ccgatatttc gatgtacaat    5760
gacagtcatg tttaagttta aaagctttaa tgactttagc catggctacc ttcgttgaag    5820
gtgcctgatc tgtaattacc ttttgaggtt taccaaattg tttaatgaga cgtttgataa    5880
acgcatatgc tgaatgatta tctcgttgct tacgcaagca aatatctaat gtatgggttc    5940
tgtaaaaatt aatactttag aaaacccagc attatatgta tcactgatat ttatattat    6000 atttcatata aatacttgaa caaaaaattc atatttaatt ttctttgttg actaacaata    6060
tttatttata agtatttgct gtcattattc taatttatgg aggccgtttt ttatgaactt    6120
taaatatttg tatgagaaat tttcttggat gagtcttgct tggattttag tgtcatgcag    6180
tgtcttaagt ggtattctga ctcccttttg ggaattccaa taggtattat tttaggctta    6240
tatttggatg gattactaaa aaaggatgct tcttgatatt aacttaattt ttaataactc    6300
cagctaatta ctgttaaagt tgtataatta ttaaattaag gaaacattac aagaaaagga    6360
aatgcatatt tgtatttcct tttcttgtaa tgttataaaa attaagatgt tataccctat    6420
ctttattaat gctataaacc gtctgccttg tgatatc                              6457
```

TREATMENT OF STAPHYLOCOCCUS INFECTIONS

RELATED APPLICATIONS

The present application is a Divisional of application Ser. No. 09/337,079, filed Jun. 21, 1999, now abandoned, the entire contents of which are incorporated herein by reference. Furthermore, this parent application (Ser. No. 09/337,079) claimed the benefit of priority of a co-pending provisional application Ser. No. 60/090,175, filed Jun. 22, 1998, the entire contents of which are hereby incorporated by reference.

BACKGROUND OF THE INVENTION

Bovine staphylococcal mastitis is a frequent problem for the dairy industry, and leads to estimated annual economic losses of $184 per cow per year. This corresponds to a U.S. total of $1.7 billion per year for milk producers and milk processors. These losses arise from reduced milk yield, reduced compositional quality, lower product quality and increased veterinary cost.

Mastitis is transmitted from cow to cow at milking time. *Staphylococcus aureus* (*S. aureus*) is a major pathogen that infects both humans and animals, and that accounts for 15 to 30% of intramammary infection cows. *Staphylococcus* infections are often characterized by their persistence and their deleterious effects on milk production and quality. Current therapies and preventative treatments for staphylococcal mastitis rely heavily on sterilization techniques, selective culling of animals with chronic recurring mastitis, and the use of β-lactam antibiotics such as cepharin and penicillin derivatives (Bramley, et al., *J. Dairy Res.*, Craven, et al., *J. Dairy Res.*, 51:513–523, 1984). Also, numerous attempts have been made to develop vaccines, but none have stood the test of time (Derbyshire and Smith, Res. Vet. Sci. 109:559, 1969; Nelson L. et al., *Flem. Vet. J.*, 62 Suppl., 1:111; Rainard et al., *Flem. Vet. J.* 62 Suppl., 1:141; Watson et al., *Proc. Int. Symp. Bovine Mastitis Indianapolis,* 73). Although sterilization techniques and the use of antibiotics have had a positive impact on dairy animal health and milk production, the prognosis for the elimination of *S. aureus* infection is poor, with often less than a 15% cure rate. This problem may be attributable to incomplete penetration of the antibiotics and/or sequestration of the bacteria within the host cells, leading to a relapse of the infection once treatment has ended (Craven and Anderson, supra). The widespread use of antibiotics in dairy animals is also of great concern to the consumer. One problem is accidental exposure of the consumer to the antibiotic drug that can induce a strong immune response and result in anaphylaxis. A second concern is that the overuse of antibiotics selects for microorganisms that are resistant to the antibiotic. Many *S. aureus* strains have already acquired resistance to commonly used antibiotics such as ampicillin and penicillin. Such prevalent problems have made it necessary to discard milk for period up to 96 hours after antibiotic treatment of an animal, resulting in an enormous waste of milk product and cost to milk producers.

There is a need for the development of an improved approach to treating mastitis infections.

SUMMARY OF THE INVENTION

The present invention provides an improved approach for the treatment of microbial infections in mammals. In particular, the invention provides methods and reagents for expressing in mammalian cells microbial proteins that have anti-microbial, particularly anti-staphylococcal, activity. The invention provides both altered genes, in which the naturally-occurring microbial sequences have been engineered to allow expression of active protein in desired mammalian cells or tissues, and methods of introducing such altered genes into desired mammalian cells and/or tissues. In certain preferred embodiments, an altered gene is modified in such a manner that the protein it encodes is not only produced in mammalian cells, but is secreted from those cells, so that a local concentration of anti-staphylococcal protein is created outside of the cells. Most preferably, such cells either are, or are in the vicinity of, cells that are targeted by infectious microbes *S. aureus* for attachment and penetration. In alternative preferred embodiments, an altered gene is prepared so that the anti-microbial protein is expressed within cells that are sensitive to intracellular infection.

The teachings of the present invention are particularly applicable to treatment of staphylococcal mastitis infections in ruminants, such as cows, goats, and sheep, and most particularly in cows. In certain preferred embodiments of the invention, the altered gene is delivered to mammary tissue in a form and through a mechanism that allows transient transfection of certain cells, preferably localized within the lining of the teat. In alternative preferred embodiments, the altered gene is delivered through the production of a transgenic animal. Any of a variety of anti-microbial agents may be employed according to the present invention, but one particularly preferred agent is lysostaphin. In preferred embodiments the natural lysostaphin gene is altered to contain one or more of a mammalian promoter, transcriptional regulatory sequence, transcriptional termination signal and/or polyA site, splicing sequences, and translation initiation sequences. Preferred altered genes also include sequences that mediate lysostaphin export from the mammalian cells in which the protein is expressed. Particularly preferred altered genes contain sequence modifications that disrupt one or more post-translational processing events that would otherwise occur upon expression of the lysostaphin protein in the mammalian cells.

DESCRIPTION OF THE DRAWING

FIG. 11 depicts the entire DNA sequence of the lysostaphin gene cloned by Recsei et al, *Proc. Natl. Acad. Sci. U.S.A.*, 84:1127–1131, 1987 (A), and the DNA sequence encoding the mature lysostaphin protein (Recsei et al., supra) (B).

FIG. 12 depicts the preprolysostaphin amino acid sequence encoded by the lysostaphin gene cloned by Recsei et al., supra.

FIG. 13 depicts the DNA coding sequence of the mature lysostaphin protein of the present invention containing 12 amino acid substitutions as compared to the Recsei et al. (supra) sequence. The modified sequence encodes a 246 amino acid protein in which all but 2 amino acids are identical to the protein encoded by the Recsei et al. (supra) sequence.

FIG. 14 depicts the DNA sequence of the β-lytic protease gene (Li et al., *J. Bacteriol.*, 172:6506–6511, 1990) (A), and the β-lytic protease amino acid sequence encoded by the β-lytic protease gene (B).

FIG. 15 depicts the lysostaphin DNA sequence cloned by Heinrich et al., (*Mol. Gen. Genet.*, 209:563–569, 1987) (A), and the amino acid sequence encoded by that gene (B).

FIG. 16 depicts the DNA sequence of the lysostaphin gene cloned by Thumm and Gotz et al. (*Mol. Microbiol.*, 23:1251–1265, 1997). The sequence presented encodes three bacterial genes. Lysostaphin is encoded by nucleotides 725–2018 of the DNA sequence.

FIG. 17 depicts the amino acid sequence of the lysostaphin gene cloned by (Thumm and Gotz et al., supra).

DESCRIPTION OF TH SEQUENCE LISTING

Figure 1:
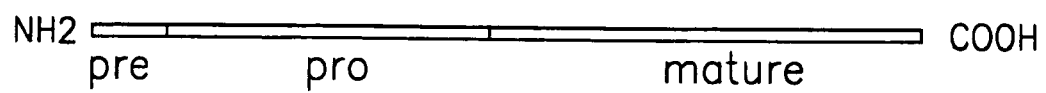
FIG. 1 is a schematic representation of the preprolysostaphin polypeptide.

SEQ ID NO:1 is the sequence of the naturally-occurring lysostaphin gene of *S. simulans* (Recsei et al, supra) (FIG. 11).

SEQ ID NO:2 is the sequence of the naturally-occurring lysostaphin protein. The sequence presented is of the preproprotein (FIG. 12).

SEQ ID NO:3 is the sequence of an inventive altered lysostaphin gene (FIG. 13).

SEQ ID NO:4 is the β-lytic protease gene from *Achromobacter lyticus* (FIG. 14).

SEQ ID NO:5 is a second sequence of a naturally-occurring lysostaphin protein (Heinrich et al., *Mol. Gen. Genet.*, 209:563–569,1987) (FIG. 15).

SEQ ID NO:6 is a third sequence of the naturally-occurring lysostaphin protein (Thumm and Gotz et al., *Mol. Microbiol.*, 23:1251–1265, 1997) (FIGS. 16 and 17).

Definitions

"Altered gene": An "altered" gene, as that term is used herein, is identical to a naturally-occurring gene except that the nucleotide sequence of the altered gene has been modified with respect to that of the naturally-occurring gene through the addition, deletion, substitution, or inversion, of one or more nucleotide residues. Preferred altered genes are those in which the coding sequence of a microbial anti-staphylococcal agent is operatively linked with mammalian expression sequences. Particularly preferred altered genes are those in which at least a portion of the microbial sequence (sufficient to encode a protein with anti-staphylococcal activity) is linked to sequences that direct the secretion of the protein from mammalian cells. Such preferred altered genes may also include sequence modifications that remove (or add) sites for post-transcriptional modifications that would otherwise occur in the mammalian cells. As will be clear to those of ordinary skill in the art, in the context of "altered gene", a "gene" includes expression signals as well as coding sequence.

"Gene": Generally speaking, a "gene", as used herein, is a single transcription unit. However, as will be clear from context and is understood in the art, the term can be used in more than one way. The "gene" for a particular protein always includes the sequence that actually encode the protein. A "gene" may also include regulatory sequences such as sites recognized by transcriptional regulators, or responsible for transcriptional termination. A "gene" may also include intronic sequences and/or splicing signals.

"Microbial host": The term "microbial host" is any self-replicating host of microscopic size that encodes within its nucleic acid genome, an anti-microbial agent. As used herein, "microbial host" can also refer to a plants and fungi that encode within their nucleic acid genome an antimicrobial agent useful in the present invention.

"Naturally-occurring": The term "naturally-occurring" is sometimes used herein to describe microbial genes encoding agents with anti-staphylococcal activity and is intended to refer to the form of the gene (i.e., the gene sequence) that is present in nature, in the microbial host in which the gene is found. Any self-replicating entity that contains nucleic acid and is found in nature can be a "microbial host" for the purposes of this definition. Moreover, although it is not generally so used in common parlance, the term "microbial host", as used herein, may refer to a plant host.

"Operatively linked": The term "operatively linked" is used herein to refer to nucleic acid sequences that are associated with one another in such a way that they are operative with respect to one another. For example, a promoter is operatively linked to a gene coding sequence when it is associated with that sequence in a manner that allows it to direct transcription of that sequence. Typically, operative linkage involves covalent attachment via a 3'–5' phosphodiester bond. Those of ordinary skill in the art will appreciate that the precise nature of the linkage may vary depending on the nature of the sequences being associated. For example, whereas a promoter is typically required to be 5' (upstream) to gene coding sequences to be operative, other transcriptional regulatory sequences (e.g., enhances) can very often exert effects from upstream, downstream, or within coding sequences, frequently regardless of orientation.

"Recombinant": The term "recombinant", as used herein, refers to a nucleic acid or protein that is produced using the established techniques of recombinant DNA technology (i.e., digestion with restriction endonuclease, ligation, site-specific DNA mutation, polymerase chain reaction, etc.). A recombinant protein is one that is produced from a gene that was made thereof, or from replicative progeny thereof.

"Regulatory sequence": A regulatory sequence is a region of DNA that, when altered or deleted, has an effect on the expression level of the gene with which it is operationally linked. Typically, regulatory sequences are regions of DNA that are recognized (i.e., bound by) protein factors that participate in the regulation of gene expression.

DETAILED DESCRIPTION OF CERTAIN PREFERRED EMBODIMENTS

Altered Anti-Staphylococcal Genes

As mentioned above, the present invention provides altered versions of microbial genes that encode agents with anti-microbial activity, the versions having been modified so that they direct expression of active protein in mammalian tissues or cells.

Those of ordinary skill in the art will appreciate that a significant number of microbial proteins, naturally found in any number of microbial hosts, are known to have anti-microbial activity. In principle, the gene encoding any such protein could be altered in accordance with the present invention. Preferred genes include those encoding anti-staphylococcal activity, for example, β-lytic protease, lysostaphin, -lytic protease, lyt-M, at1ALE-1, zooA. Other preferred anti-microbial peptides or proteins whose genes could be utilized include lysozyme, nisin, muramidases, glucoasminidases, and colicins. (see, for example Shockman and Barrett, *Proc. Natl. Acad. Sci. U.S.A.,* 51:414–421, 1964; Yamada et al., *J. Bacteriol.,* 178:1565–1571, 1996). Particularly preferred are genes encoding bacteriocins, which are peptide antibiotics that are produced by bacteria and are effective against even closely related species but do not have significant deleterious effects on the species that produces them or on eukaryotic cells. One particularly preferred bacteriocin gene is the lysostaphin gene.

Altered Lysostaphin Genes

Lysostaphin is naturally produced by *Staphylococcus simulans*. Lysostaphin kills closely related staphylococcal species, but does not harm other bacterial species or eukaryotic cells. Lysostaphin has endopeptidase activity and kills cells by hydrolyzing the pentapeptide links of staphylococcal cell walls, causing the cells to lyse (Schindler and Schuhardt, *Proc. Natl. Acad. Sci. U.S.A.,* 51:414–421, 1964). If injected directly into the mammary gland of mice or dairy cattle, recombinant lysostaphin is protective against staphylococcal infection (Bramley and Foster, *Res. Vet. Sci.,* 49:120–121, 1990; Oldham and Daley, *J. Dairy. Sci.,* 74:4175–4182, 1991). The minimum inhibitory concentrations of recombinant lysostaphin against *S. aureus* are less than 100 ng per ml in culture media and less than 2 μg per ml in milk, (Bramley and Foster, *Res. Vet Sci.,* 49:120–121, 1990; Oldham and Daley, *J. Dairy Sci.,* 74:4175–4182, 1991). This low concentration requirement makes lysostaphin an attractive candidate for the prevention and treatment of mastitis, because one requirement of the present invention is that the protein be expressed and secreted at sufficient concentrations in vivo to kill *S. aureus.*

The gene encoding lysostaphin is naturally found on a large plasmid in *S. simulans*, and encodes a preproenzyme that is processed extracellularly to a mature form, which is active (FIG. 1). Several allelic variations of this gene have been identified that are apparently found in nature (Heinrich et al., supra, (SEQ ID NO: 9) (FIG. 15A); Recsei et al., supra, (SEQ ID NO: 1) (FIG. 11); Thumm and Gotz et al., supra, (SEQ ID NO: 10) (FIG. 16); U.S. Pat. No. 4,931,390). The sequence of mature lysostaphin identified by Heinrich, (et al., supra) differs from the sequence identified by Recsei, (et al. supra) by one amino acid, whereas preprolysostaphin has multiple differences. Furthermore, the preprolysostaphin sequence identified by Thumm and Gotz et al., (supra)

differs from the preprolysostaphin sequence identified by both Recsei (et al., supra) and Heinrich (et al., supra). According to Thumm and Gotz (et al., supra), preprolysostaphin is 493 amino acids having a signal peptide of 36 amino acids, a propeptide of 211 amino acids and a mature lysostaphin protein of 246 amino acids.

In the present application the term "mature form" refers to a lysostaphin protein which has had the propeptide cleaved off. It should be noted, however, that "active forms" of lysostaphin are not limited to the mature form; other unprocessed forms of lysostaphin also have activity. In particular, preprolysostaphin and prolysostaphin. Prolysostaphin is bioacitve, but mature lysostaphin is 4.5 times more bioactive than prolysostaphin (Thumm and Gotz et al., supra). Variations of lysostaphin that can be modified to be expressed in an active form in mammalian cells fall within the scope of the presently claimed invention.

In order to prepare an altered lysostaphin gene according to the present invention, the naturally-occurring lysostaphin gene sequence must be modified to allow for expression of active lysostaphin protein in mammalian cells. As will be appreciated by those of ordinary skill in the art, expression of bacterial proteins in mammalian cells is often not trivial. Typically, the bacterial coding sequence must be operatively linked to a mammalian, or at least a eukaryotic, promoter and a eukaryotic translation initiation sequence. Although it is often not required that every nucleotide of coding sequence be preserved, or that the coding sequence initiate and terminate at precisely the same points as it does in its natural host system (fusion proteins and modest deletions are usually tolerated), it is essential that the coding sequence to be employed be operatively linked to expression signals that are effective in the cells into which the altered gene is to be introduced.

A large number of different eukaryotic, and particularly mammalian, expression signals are known in the art and include promoters, transcriptional regulatory sequences (often provided in conjunction with the promoter with which they are naturally associated, or with a promoter with which they have previously been experimentally associated), transcriptional termination signals, splicing signals, translation initiation signals, post-transnational processing signals, and secretory signals (see, for example, *Current Protocols* 16.0–16.21.9). Those of ordinary skill in the art will appreciate that not every one of such signals must be employed in an altered gene of the present invention. It is generally preferred to include eukaryotic (preferably mammalian) transcription and translation initiation signals; other sequences may be employed as necessary or desirable. Various other modifications may also be made.

Promoters that may be employed include constitutive promoters, inducible promoters, universal promoters (i.e., active in substantially all cell types), and/or tissue specific promoters. Those of ordinary skill in the art will appreciate that the precise application of the inventive altered gene will determine which category of promoter is more desirable. For example, if expression is desirably limited to a particular tissue, a tissue-specific promoter is employed; if expression is desirably limited to times when certain environmental conditions are present, an inducible promoter responsive to those environmental conditions is employed. Particular promoters are also selected on the basis of their ability to direct higher or lower levels of transcription.

As mentioned above and discussed more fully below, in certain preferred embodiments of the present invention, an altered lysostaphin gene is to be expressed in mammary tissue. If the altered gene is to be introduced only into mammary cells, a tissue-specific promoter is not required. Preferred promoters for use in such circumstances include, but are not limited to, Cytamegalovirus, (CMV), Rous Sarcoma Virus (RSV) and human elongation factor 1 (EF-1) λ subunit. Particularly preferred is CMV. Of course, a tissue-specific promoter may nonetheless be employed. Known mammary-specific promoters include, for example, β-lactoglobulin, λ-lactalbumen, caseins and whey acidic protein. Particularly preferred is the β-lactoglobulin promoter.

The Kozak sequence is well established to be the eukaryotic translation initiation sequence and is the preferred sequence to be introduced into altered genes of the present invention.

Williamson and colleagues have previously reported that operative linkage of the entire lysostaphin gene to the human cytomegalovirus promoter and the Kozak initiation sequence is sufficient to direct expression of lysostaphin in COS-7 cells, but active enzyme was not secreted from the cells (Williamson et al., *Appl. Environ. Microbiol.*, 60:771–776, 1994). The low level of activity detected by Williamson, et al., supra (less than 1 ng/ml), is likely due either to release from lysed cells and a small amount of protein that escapes glycosylation in the in vitro system.

Figure 2:
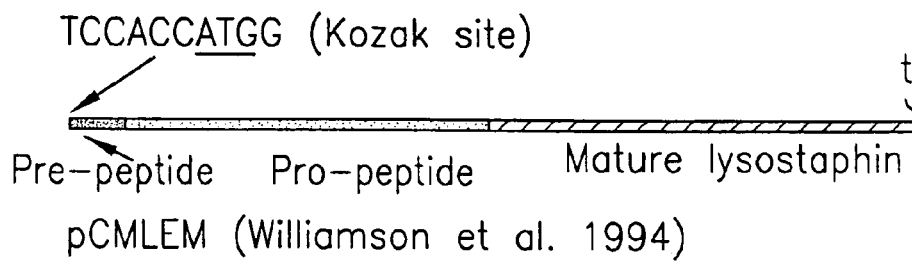
FIG. 2 is a representation of modifications of the lysostaphin gene for eukaryotic expression.
Figure 2:
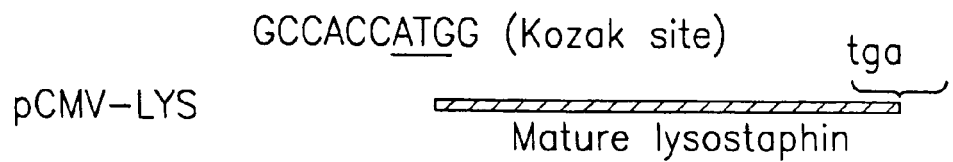
Figure 2:
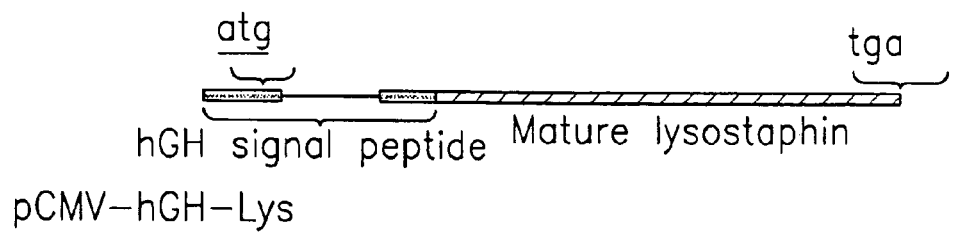
Figure 2:
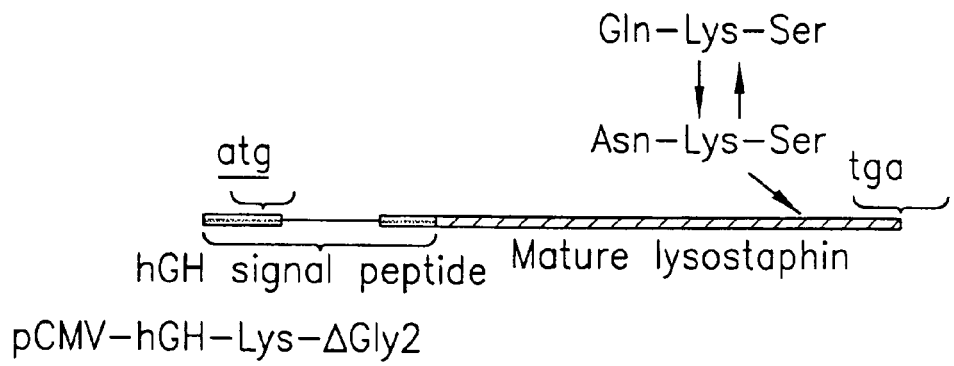
Figure 2:
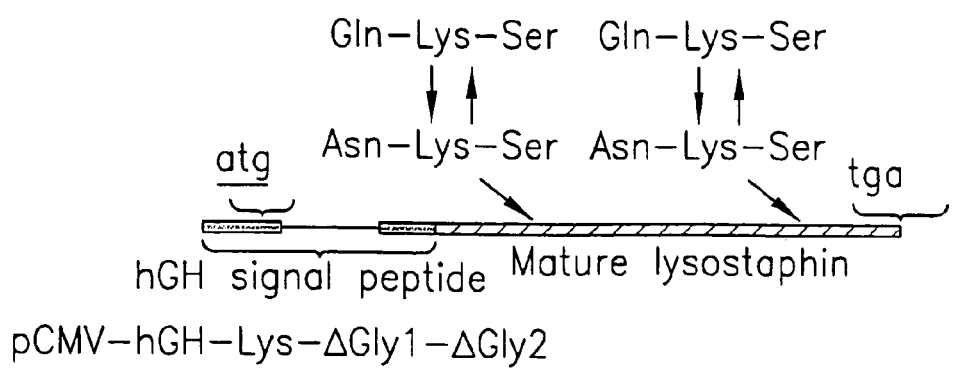
Figure 3:
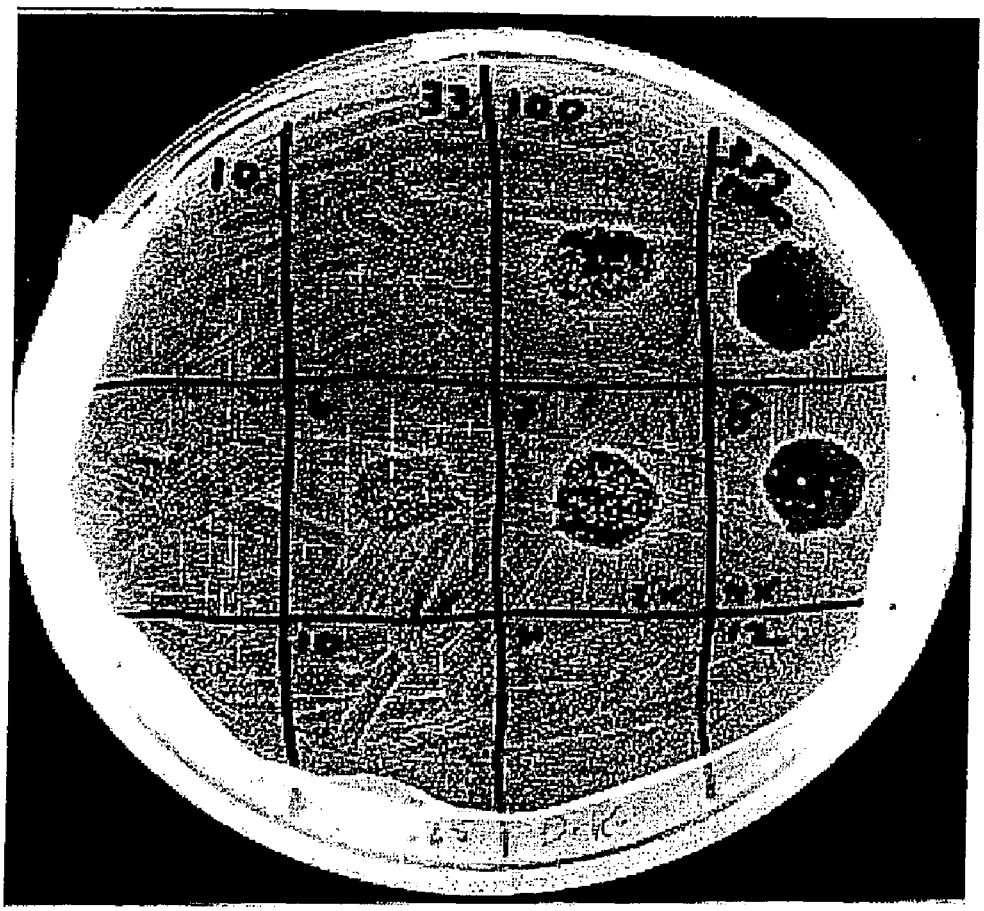
FIG. 3 is an experiment demonstrating lysis of *S. aureus* by bioacitve lysostaphin produced by COS-7 cells transfected with pCMV-Lys. Conditioned media or cell extracts were lyophilized and resuspended with the original volume (1×), 0.5 volume (2×), or 0.25 volume (4×) of $H_2O$. Lysostaphin standards were prepared in media. Samples or standards (15 μl) were then applied to an LB agar plate freshly streaked with *S. aureus* and incubated 16 hr, 37° C. Top row, lysostaphin standards at concentrations of 10, 33, 100, and 333 μg/ml; middle row, blank, 1×, 2×, 4× cell extract; bottom row, blank, 1×, 2×, 4× conditioned media.

As described in Example 1 and FIG. 2, we have prepared an altered version of the lysostaphin gene that directs production and secretion of active lysostaphin from mammalian cells. Our first attempt at producing an active, secreted lysostaphin in mammalian cells utilized a construct, pCMV-Lys, in which the coding sequence for mature lysostaphin was operatively linked to the cytomegalovirus promoter and the bovine growth hormone polyadenylation signal. This construct, like that described by Williamson et al., was sufficient to produce lysostaphin in mammalian cells, but did not produce active secreted protein (FIG. 3).

In an effort to correct this problem, we produced a second construct, pCMV-hGH-Lys, that included a mammalian signal peptide to direct secretion of the lysostaphin protein from the cell. Those of ordinary skill in the art will appreciate that any of a number of different signal peptides could have been used including, but not limited to, β-lactoglobulin, caseins, erytropoietin, and insulin, so long as they were linked in-frame to the lysostaphin coding sequence. We elected to use the human growth hormone signal peptide, because expression and secretion of the entire human growth hormone gene had previously been demonstrated in the ruminant mammary gland (Kerr et al., *Anim. Biotechnol.* 7:3345, 1996); moreover, the human growth hormone signal peptide had previously been used to direct the secretion of engineered proteins from Chinese hamster overy cells (Pecceu et al, Gene, 97:253–258, 1991).

Figure 4:
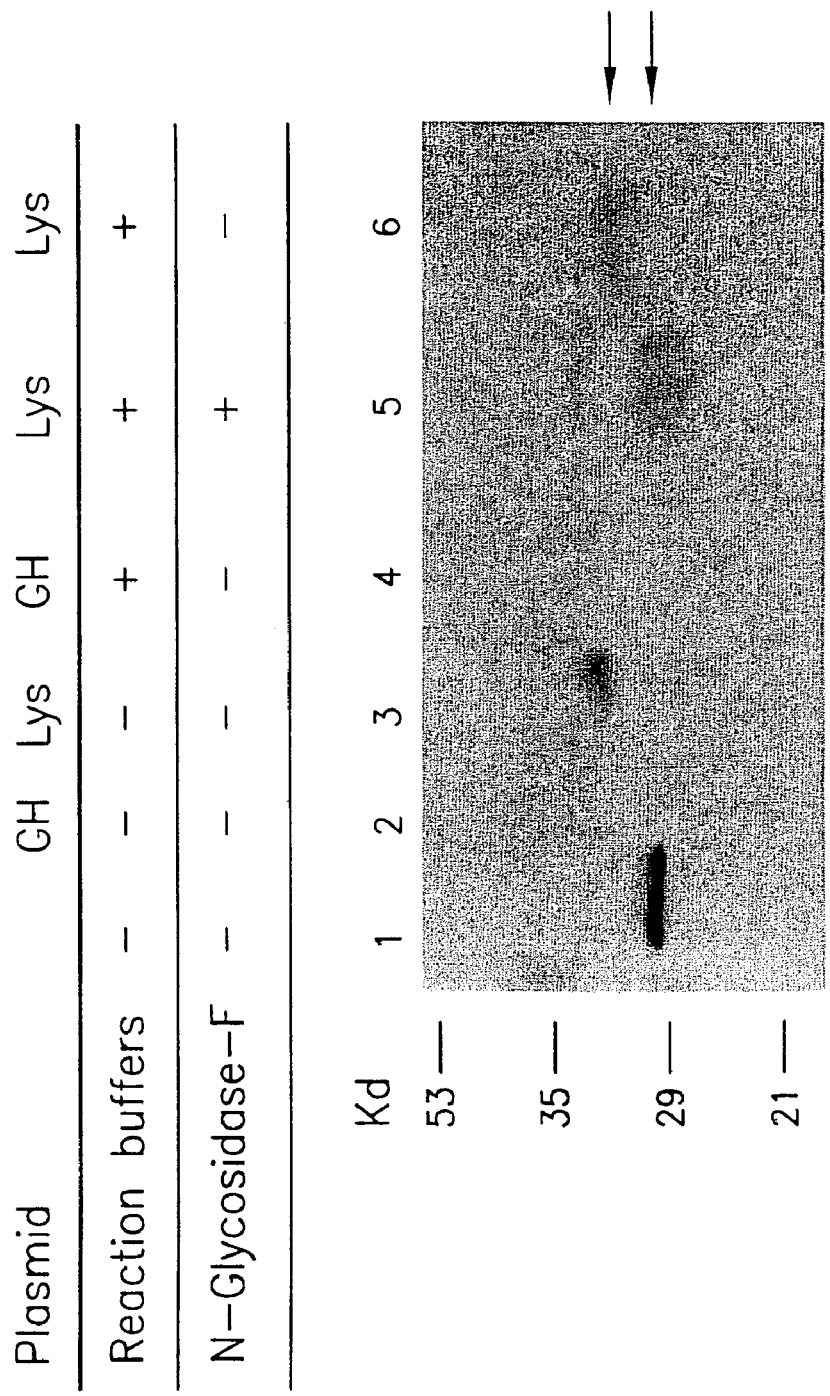
FIG. 4 is a Western blot analysis of conditioned media samples treated with or without N-glycosidase-F. Molecular size standards are shown on the left. Samples in lanes 1,2, and 3 were untreated, and contain 20 μl of media from COS-7 cells transfected with: pCMV-hGH control, spiked with 1 μg/ml lysostaphin (lane 1), PCMV-hGH control (lane 2), pCMV-hGH-Lys (lane 3). Samples in lanes 4 and 6 were incubated with deglycosylation buffers, no enzyme, for 16 hr, 37° C. Sample in lane 5 was incubated with deglycosylation buffers, and enzyme, for 16 hr, 37° C. Lanes contain 20 ul of media from COS-7 cells transfected with; pCMV-hGH (lanes 4), pCMV-hGH-Lys (lanes 5, 6).

In analyzing the inactive lysostaphin produced from our second construct, we noted that it had a molecular weight of approximately 33 Kd, somewhat larger than the lysostaphin standard that migrated at 28 Kd (FIG. 4). We hypothesized that post-translational processing events, in particular glycosylation events, might be disrupting the activity of the lysostaphin produced in mammalian cells. Other post-translational processing events that might affect biological activity include methylation, disulfide bond formation, acetylation, phosphorylation and sialylation. As those of ordinary skill in the art will appreciate, bacterial proteins are not normally glycosylated. However, when such proteins are expressed in a mammalian system, there is the possibility that the mammalian cell will recognize putative glycosylation steps within the sequence of the bacterial protein, and will add glycosyl groups that may alter the activity of the protein. Glycosylation of lysostaphin during secretion inactivates the lysostaphin protein. Consequently, it may be desirable to modify the potential glycosylation sites to prevent deactivation of the lysostaphin protein by glycosylation during secretion.

We scanned the lysostaphin protein sequence for possible glycosylation sites that might be recognized in a mammalian expression system. We identified two instances of the sequence Asn-X-(Ser/Thr), which can be recognized by mammalian N-linked glycosylation machinery. We confirmed that exposure of the protein to N-glycosidase F, which removes N-linked glycosyl groups, reduced the apparent molecular weight of the protein to that of the lysostaphin standard (FIG. 4).

In light of these findings, we prepared new constructs in which we had modified one or both of the N-linked glycosylation sites by substituting Gln for Asn (FIG. 2). Those of ordinary skill in the art will recognize that any of a variety of other approaches could be used to disrupt a potential N-linked glycosylation site, but substitution is generally preferred over addition or deletion of residues; conservative substitutions (i.e., substitutions with amino acids of comparable chemical characteristics) are particularly preferred. For the purposes of conservative substitution, the non-polar (hydrophobic) amino acids include alanine, leucine, isoleucine, valine, glycine, proline, phenylalanine, tryptophan and methionine. The polar (hydrophilic), neutral amino acids include serine, threonine, cysteine, tyrosine, asparagine, and glutamine. The positively charged (basic) amino acids include arginine, lysine and histidine. The negatively charged (acidic) amino acids include aspartic acid and glutamic acid.

We found that removal of both glycosylation sites resulted in production of an active, secreted lysostaphin from mammalian cells (see Example 5 and Example 1). We note that this observation of active lysostaphin secreted from mammalian cells is the first such demonstration. In fact, prior work evidences the difficulty of achieving active secreted protein. In particular, WO 96/35793, reports detection of very large amounts (100 to 250 ng/ml/24 hr) of lysostaphin protein in cell extracts, but little or no activity of that material. Accordingly, an "altered lysostaphin gene" of the present invention is a lysostaphin gene whose sequence has been modified as compared with that of naturally-occurring lysostaphin (SEQ ID NO:3) in that lysostaphin coding sequence sufficient to encode at least mature lysostaphin has been (i) operatively linked to mammalian expression signals sufficient to direct expression of the gene product in mammalian cells; (ii) operatively linked to a mammalian signal peptide such that the expressed gene product is secreted from the mammalian cells in which it is produced, and, preferably, (iii) modified such that at least one, and preferably both, of the Asn-X-(Ser/Thr) N-linked glycosylation sites is disrupted. Alternatively, it may be desirable to eliminate the signal peptide to permit intracellular accumulation of the anti-microbial protein.

As mentioned above, the lysostaphin coding sequence that is useful in the production of altered lysostaphin genes according to the present invention is not limited to the mature lysostaphin sequence; the preprolysostaphin and prolysostaphin sequences have also been shown to produce active proteins, although expression of the inmature form of lysostaphin is substantially less than that of the mature form. Moreover, as will be appreciated by those of ordinary skill in the art, various changes to the precise lysostaphin amino acid sequence can readily be made without interfering with (and sometimes promoting, as seen in the glycosylation site examples) lysostaphin activity. So long as the lysostaphin amino acid sequence does not differ so extensively from that presented as SEQ ID NO:2 that activity is lost, the sequence may be used in accordance with the present invention. Those of ordinary skill in the art are well familiar with techniques for modifying amino acid sequences (see, for example, Sambrook, J. et al., *Molecular Cloning: A Laboratory Manual*, Cold Spring Harbor Press, N.Y., incorporated herein by reference), and may employ any known technique, including those described herein, to assay the proteins produced from genes containing such modifications in order to determine whether such genes encode functional proteins as required by the present invention. Altered genes that direct expression and serection of an active lysostaphin protein with one or more sequence differences from naturally-occurring lysostaphin (SEQ ID NO:1) or from the particular altered lysostaphin described herein (SEQ ID NO:3) are considered to be "functional equivalents" of the altered lysostaphin described herein, and are within the scope of the present invention.

Additional modifications to the lysostaphin gene that fall within the scope of the present invention include, for example, nucleotide substitutions that more accurately reflect eukaryotic codon usage without altering the amino acid sequence of the encoded protein (see, for example, Sambrook, et al., supra). Such changes are expected to enhance the efficiency of translation and the amount of protein being produced. Another modification involves removal or disruption of a potential polyadenylation signal near the 3' end of the lysostaphin gene.

Altered β-Lytic Protease Genes

Another preferred bacterial gene for use in the production of altered genes according to the present invention is the β-lytic protease gene (SEQ ID NO:4) from *Achromobacter lyticus* (Li et al., *J. Bacteriol.*, 172:6506–6511, 1990). β-lytic protease exhibits potent bacteriolytic activity on *Micrococcus lysodeikticus* and *S. aureus*. It is approximately 25-fold more potent than lysostaphin on heat killed *S. aureus*, and approximately 40-fold more potent than lysostaphin on viable *S. aureus* (Li et al., *J. Biochem.* (Tokyo), 122: 772–778, 1997).

An altered β-lytic protease gene according to the present invention is produced, as was the case with the lysostaphin gene, by operatively linking β-lytic protease coding sequence with (i) a mammalian promoter; (ii) a mammalian translation initiation sequence; and (iii) a mammalian signal peptide. Additional modifications may also be made.

Other Altered Genes

Any of a variety of other genes encoding agents with anti-microbial activity may also be employed in accordance with the present invention. As discussed above, a variety of different microbial anti-staphylococcal agents are known. Any gene encoding such an agent may be modified as described herein to produce an altered gene of the present invention. Useful genes may be isolated from any natural source, including bacteria, fungi, plants, and other microbes.

These other anti-staphylococcal genes are modified to produce altered genes of the present invention through operative linkage with (i) a mammalian promoter; (ii) a mammalian translation initiation sequence; and (iii) a mammalian signal peptide. Additional modifications may also be made. For example, some such genes may have introns, or sequences that are recognized as introns, that are inappropriately spliced in a mammalian system. Such inappropriate splicing events can be identified, for example, by isolating mRNA from a mammalian cell transfected with a version of the gene that has been modified to include the mammalian promoter, translation initiation sequence, and signal peptide. Inappropriate splicing may be corrected by alteration of inappropriate splice sites, or removal of intronic sequences. However, it is often desirable to maintain (or introduce) at least one intron in an altered gene, as intron-containing genes are often more efficiently expressed in mammalian systems (see, for example, Wall and Seidel, *Theriogenology*, 38:337–357).

Also, the mammalian signal peptide might not be properly cleaved from the protein produced upon expression of a modified gene containing a mammalian promoter, translation initiation sequence, and signal peptide in a mammalian cell. Inappropriate signal peptide cleavage may be identified by immunopurification of the expressed protein, which is then analyzed by polyacrylamide gel electrophoresis and/or N-terminal sequencing. Problems with signal peptide cleavage can generally be corrected through selection of a different signal peptide, such as one from one of the major milk proteins.

Additionally, as discussed above, modifications may be made to introduce mammalian codons without changing protein sequence, to remove or disrupt any putative glycosylation sites and/or polyadenylation signals, etc.

Finally, those of ordinary skill in the art will recognizes that the principles taught by the present invention are readily applicable to genes encoding proteins or peptides with anti-microbial (including anti-viral) activity other than, or in addition to, anti-staphylococcal activity. For example, as mentioned above, *Staphylococcus aureus* accounts for up to only 30% of intra-mammary infections (Nickerson et al, *J. Dairy Sci.*, 78:1607–1618, 1995). It will be clear to one skilled in the art that the other 70% of intra-mammary infections are due to other pathogens and therefore any protein with anti-bacterial activity that would combat the offensive pathogen could be delivered to the mammary gland for treatment of mastitis. Furthermore, multiple genes could be delivered to the mammary gland simultaneously (see further discussion below).

Introduction of Altered Genes into Mammalian Expression Systems

The altered anti-microbial genes of the present invention may be introduced into mammalian cells or tissues in order to treat or prevent infection of those tissues. In vitro transfection methods that introduce DNA into mammalian cells in culture are well known in the art, and include calcium phosphate transfection, DEAE-dextran transfection, electroporation, and liposome-mediated transfection.

In the present invention, it is preferred that the method of protein expression utilize methods that transfer DNA into living cells in vivo. In certain embodiments, the genes are delivered by somatic cell engineering, or gene therapy. In such circumstances, the genes are not delivered to the animal's offspring, and are often (unless retroviral delivery systems are employed) only transiently expressed in the cells to which they are delivered.

A variety of systems are available for delivering altered genes to somatic cells, either systemically or locally, in accordance with the present invention (see, for example, Ausubel et al., *Current Protocols in Molecular Biology*, Greene Publishing Associates, New York, V. 1&2, 1996 and Kerr et al., *Anim. Biotechnol.*, 7:33–45, 1996). Such systems include, but are not limited to, high-pressure jet injection, lipisome-based delivery systems, and viral delivery systems, including both retroviral and standard viral systems.

The mammalian cells and tissue into which altered genes of the present invention are to be produced include any mammalian cells or tissues. Preferred cells are tissues within ruminants such as cows, sheep and goats, but also include human tissues. Also, although mammary tissue is one particularly preferred tissue for expression (see below), any tissue that is susceptible to, or that is experience, microbial infection, is a desirable expression site according to the present invention.

Notwithstanding the foregoing, expression in mammary tissue is a particularly preferred aspect of the present invention. Thus, in preferred embodiments of the invention, the delivery system is selected, in combination with the gene modifications, to ensure that the altered gene is expressed in mammary tissue. In one particularly preferred embodiment, an altered anti-staphylococcal gene is delivered locally to mammary epithelial cells via the teat canal. This route of intramammary infusion administration has the greatest chance of transfecting the epithelial cells lining the teat or teat duct, which are a prime target for attachment and invasion by staphylococcal species and therefore are also an important target for the production of anti-microbial proteins. Alternatively, in another preferred embodiment delivery of plasmid DNA into lactating sheep mammary parenchyma can be achieved by high-pressure jet-injection. This method achieves transfection of cells within the narrow path of the injectate (Kerr et al., *Anim. Biotechnol.*, 7:33–45, 1996).

Altered anti-staphylococcal genes can be delivered to the epithelial cells of the mammary gland by non-viral approaches (Hyde et al., *Nature*, 362:250–255, 1993; Oudrhiri et al., *Proc. Natl. Acad. Sci. U.S.A.*, 94:1651–1656, 1997; Hens et al., *Molec. Biol. of Cell, Suppl,* 1996). Non-viral approaches generally rely on liposome carriers to enhance transfection efficiency. For example, transfection of guinea pig mammary gland with the human growth hormone gene resulted in accumulation of up to 500 ng/ml of the human growth hormone in milk (Hens et al., supra).

In other preferred embodiments of the present invention, viral vector approaches are utilized to achieve transient transfection of mammary epithelial cells with inventive altered genes. Viral vector approaches include retro- (Kay et al., *Science*, 262:117–119, 1993), adeno- (Smith et al., *Nat. Genet*, 5:397–402, 1993) and adeno-associated viruses (Flotte, *J. Bioener. Biomembr.*, 25:37–42, 1993). Retrovirus infection results in integration of the viral nucleic acid code into the host cell DNA, causing permanent transfection of that cell. Retroviruses can only infect dividing cells, but have been shown to be capable of transfecting the caprine mammary gland during a period of hormone-induced mammogenesis (Archer et al., *Proc. Natl. Acad. Sci. U.S.A.*, 91:6804–6844, 1994). In a particular preferred embodiment, an adenovirus vector is used to deliver altered anti-staphylococcal genes to bovine mammary epithelial cells. The adenoviral-based method of gene delivery has several advantages over retroviral-based gene delivery in that transfection efficiency is higher, and it can infect non-dividing cells. New adenoviral vectors have also been developed that limit the host antiviral immune response which is common to adenoviral transfection. A strong cellular immune response can greatly reduce the persistency of andenoviral-mediated gene expression and precludes repeated administration of the same vector (Ilan et al., *Proc. Natl. Acad. Sci. U.S.A.*, 94:2587–2592, 1997; Chen et al., *Proc. Natl. Acad. Sci. U.S.A*, 94:1645–1650, 1997; Smith et al., supra). We have demonstrated that an adenoviral vector systems can be successfully employed for delivery of genes to the ruminant mammary (Plaut et al, *J. Dairy Sci.*, 80, Suppl. 1, 155 (Abstract), 1997) (see Example 2). Direct administration of adenovirus containing the β-galactosidase gene to the teat of a goat resulted in intense blue staining of the entire lining of the teat canal (see FIG. 7). Mammary tissues were also infected. This finding is readily generalizable to the inventive altered genes, which may therefore also be delivered to ruminant mammary cells through adenoviral transfection (see Example 3).

Those of ordinary skill in the art will appreciate that it will sometimes be desirable to express more than one inventive altered gene simultaneously in the same mammalian cells or tissue. With this multi-gene approach, not only is the spectrum of the bactericidal activity improved, but the likelihood of bacterial resistance development is substantially diminished.

Transgenic Animals

The altered genes of the present invention may also be introduced into mammalian cells through transfer into mammalian germ line cells and subsequent production of transgenic animals. Established methods for such germ line transfer include, but are not limited to, micro injection of DNA into one-cell embryos (Gordon et al., *Proc. Natl. Acad. Sci U.S.A.*, 77:7380–7384, 1980), transfer of genetically engineered embryonic stem-cells into blastocysts (Hooper et al, *Nature*, 326:292–295, 1987; Kuehn et al, *Nature*, 326: 295–298, 1987), and the transfer of nuclei from engineered cells into enucleated oocytes (Campbell et al, *Nature*, 380: 64–66, 1996). Germ genetically engineered cells to oocytes, (Schnieke et al., *Science*, 278:2130–2133, 1997) results in a permanent change in the animal's genome, and the genomes of its offspring.

Germ cell engineering has become wholly routine in the area of transgenic mice (Gordon et al., *Biotechnology*, 5:1183–1187, 1987), and has also been broadly applied to pigs (Wall et al., *Proc. Natl. Acad. Sci. U.S.A*, 88:1696–1700, 1991), sheep (Wright et al., *Biotechnology*, 9:830–834, 1991), goats (Ebert et al., *Biotechnology*, 9: 835–838, 1991), and cattle (Krimpenfort et al., *Biotechnology*, 9:844–847, 1991). To give but one relevant example, Gordon et al., (*Biotechnology*, supra) have created transgenic mice that produced human tissue plasminogen activator in transgenic mouse milk. Any of the techniques described in these references, or otherwise known in the art, may be employed to create transgenic animals in which an altered gene of the present invention has been stably introduced into their genome. Such transgenic animals are useful not only as *staphylococcus*-resistant creatures, but as bioreactors for the production of anti-staphylococcal agents for use in the treatment of others.

Peptide Antibiotics

Peptide antibiotics are widespread in nature, being found in plants, animals and prokaryotes. Animal antibacterial proteins include lysozyme, lactoferrin, and a class of antimicrobial compounds known as defensins. Lysozyme is a muramidase to which Gram negative and some Gram positive microorganisms such as *S. aureus* show varying degrees of resistance (for reviews, see Reiter, et al., *International Dairy Federation Bulletin* #191 IDF, Square Vergote 41, 1040—Brussels, Belgium; Magga and Murray, *J. Dairy Sci.*, 78:2645–2652, 1995). It is normally present in human milk at approximately 100 µg per ml and in ruminant milk at less than 1 µg per ml, yet the role lysozyme may play in the prevention of mastitis is presently unknown. However, lactoferrin, which acts as an antimicrobial through its iron-chelating activity, (Reiter et al, supra), does protect the non-lactating mammary gland from infection by *E. coli*, although this inhibition is lost at the time of calving (Bramley, *J. Dairy Res.*, 43:205–211, 1976). Furthermore, the defensins, produced in neutrophils, macrophages and epithelial cells lining mucosal surfaces (Kagan et al., *Toxicology*, 87:131–149, 1994), also have antibacterial action resulting from their ability to form pores in susceptible cellular membranes. One particular defensin, bovine tracheal antimicrobial peptide, (TAP), has antibacterial activity in vitro against *E. coli* and *S. aureus*, with minimum inhibitory concentrations (Diamond et al., *Proc. Natl. Acad. Sci. U.S.A.*, 88:3952–3956, 1991) and would therefore be a likely candidate for use in the present invention.

EXAMPLES

The present invention can be further understood through consideration of the following non-limiting Examples.

Example 1

Genetic Engineering of the Lysostaphin Gene

A. Construction of New Lysostaphin Expression Plasmids

In an attempt to increase production and secretion of lysostaphin four new expression constructs were prepared (FIG. 2). All four constructs were made by inserting modified lysostaphin genes into the polylinker of the 5.4 Kb eukaryotic expression vector, pcDNA3 (Invitrogen). The vector contains the CMV promoter and the bovine GH polyadenylation signal, with an intervening polylinker.

All four lysostaphin constructs were generated by a PCR-based technique in which the 5' primer included a 5' Not I restriction site and the 3' primer included a 3' Apa I site. The primers were positioned such that only the coding region and the TGA stop codon of the mature portion of the lysostaphin gene were amplified. We used pCMLEM (Simmonds et al., *Appl. Environ. Microbiol.*, 62:4536–4541, 1996) as the lysostaphin template, and the resulting Not 1-Lysostaphin-Apa I amplicons were cloned between the Not I and Apa I sites in the pcDNA3 polylinker. The nucleotide sequences of all PCR-generated fragments were confirmed with an automated cycle-sequencing technique at the University of Vermont molecular diagnostics laboratory.

The expression plasmid pCMV-Lys was constructed by inserting a short linker sequence 5' to the mature lysostaphin sequence, between the Bam HI and Not I sites of the pcDNA3 polylinker. The short sequence was prepared from two custom 13 base oligonucleotide (Gibco/BRL), and resulted in the addition of a Kozak sequence and a start codon (ATG) to the lysostaphin gene. These features, that are required for efficient translation initiation, encode the insertion of an additional N-terminal amino acid (methionine) to the lysostaphin protein. This engineered protein does not contain a signal peptide and thus would not be transferred to the golgi apparatus for glysosylation and secretion.

The expression plasmid pCMV-hGH-Lys was constructed by inserting the human growth hormone (hGH) intron-containing signal peptide coding region, 5' to the mature lysostaphin sequence. This eukaryotic signal peptide was chosen to enhance the secretion of lysostaphin from the cells. We have previously had satisfactory experience with the expression of the entire hGH gene in the ruminant mammary gland (Kerr et al., *Anim. Biotechnol.*, 7:33–45, 1996), and it has been used by others to direct the secretion of engineered proteins (Pecceu et al., *Gene*, 97:253–258, 1991). The coding region of the hGH signal peptide included the 5' untranslated region and the first intron of the hGH gene. The intronic sequence was included as there is good evidence that introns increase expression of foreign proteins (Wall and Seidel, Jr., *Theriogenology*, 38, 337–357, 1992). The modified hGH signal peptide was obtained from a collaborator (Dr. K. Wells, GEML-ARS-USDA, Beltsville, Md.). The resulting hGH-lysostaphin sequence codes for the amino acids of the entire hGH signal peptide immediately followed by the entire mature form of lysostaphin. The sequence of this construct was confirmed by DNA sequencing.

The expression plasmids pCMV-hGH-Lys-ΔGly2 and pCMV-hGH-Lys-ΔGly1-ΔGly2 were subsequently prepared. A PCR strategy was used to remove glycosylation sites from the mature lysostaphin gene and generate pCMV-hGH-Lys-ΔGly2 and pCMV-hGH-Lys-ΔGly1-ΔGly2. pCMV-hGH-Lys-ΔGly2 removes one of two potential N-linked glycosylation sites within mature lysostaphin. The final construct, pCMV-hGH-Lys-ΔGly1-ΔGly2, was designed to encode a lysostaphin protein in which both N-linked glycosylation sites (Asn-X-Ser/Thr) have been removed by mutation of the site's Asn codons to Gln codons (FIG. 2). Bacterial proteins are not normally glycosylated, but when expressed in a eukaryotic system, any Asn-Xxx-Ser/Thr sequence of amino acids in a protein has the potential for N-linked glycosylation. The plasmids pCMV-hGH-Lys-ΔGly2 and pCMV-hGH-Lys-ΔGly1-ΔGly2, was constructed in a similar fashion to pCMV-hGH-Lys. However, the 3' primer for generating the lysostaphin amplicon contained nucleic acid substitutions that resulted in a change from AAT to CAG at the codon for amino acid number 232 of the mature lysostaphin protein. This causes an asparagine to glutamine change in the encoded protein, and thus destruction of the potential glycosylation site. We chose to convert Asn to Gln based on the similar structure and characteristics of their side groups. The plasmid pCMV-hGH-Lys-ΔGly1-ΔGly2 was similarly constructed using a synthetic 5' primer. The Asn to Gln strategy was recently reported as being successful in preventing the glycosylation of a bacterial enzyme that was engineered to be expressed on the cell surface of eukaryotic cells (Marais et al., *Nat Biotechol*. 15:1373–1377, 1997). Importantly, these authors reported considerable enzymatic activity of the modified protein was maintained, even with three Asn to Gln mutations.

B. Evaluation of Lysostaphin Expression Plasmid In Vitro

Figure 7A:
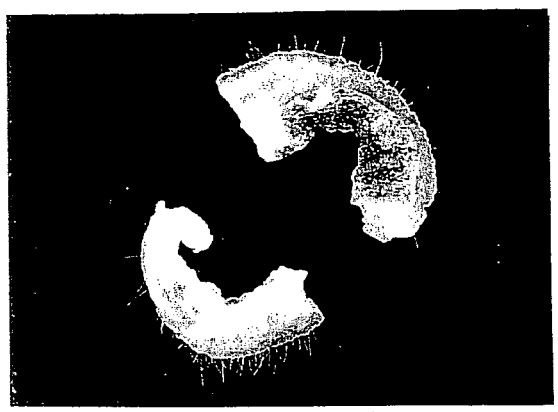
FIG. 7 shows tissue fragments, tissue section and cultured cells, exposed to the X-gal reagent for visualization of β-galatosidase activity (panel A–E). (A) Teat tissue, (B) adjacent mammary tissue, (C) sections of teat tissue (40×), (D) primary culture of mammary tissue from one goat mammary gland transfected with LacZ-containing adenovirus (Av1 Lac4) by intrammary infusion. The contralateral gland was infused with vehicle and blue staining was not observed (lower tissue pieces panel A and B). (E) Bovine mammary epithelial cell line (BME-UV) following transfection with AvLacZ4. (F) Green fluorescent protein in COS-7 cells transfected with the GFP gene.
Figure 7B:
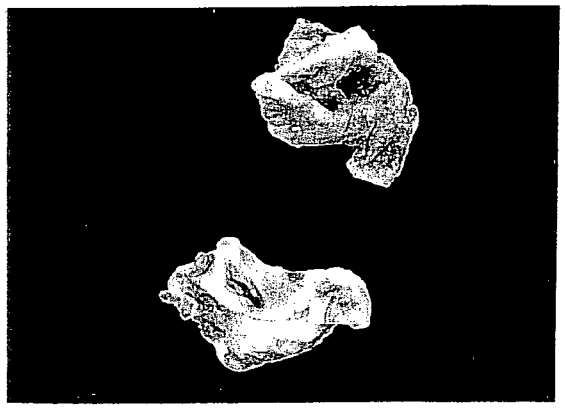
Figure 7C:
Figure 7D:
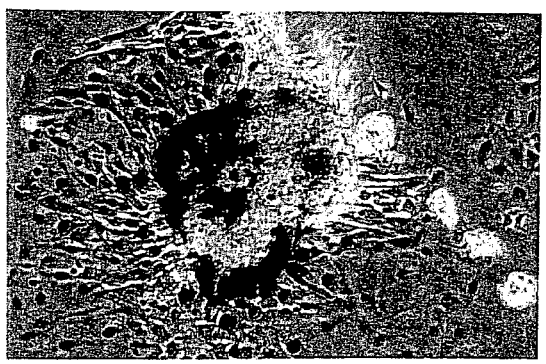
Figure 7E:
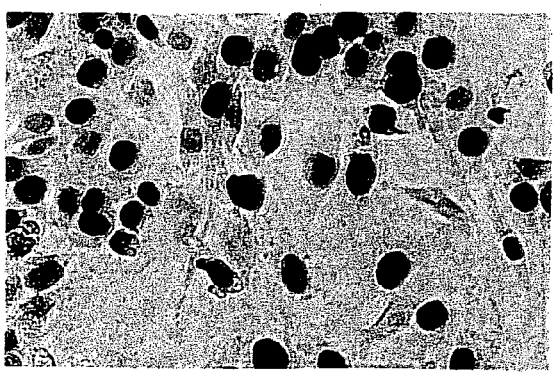
Figure 7F:
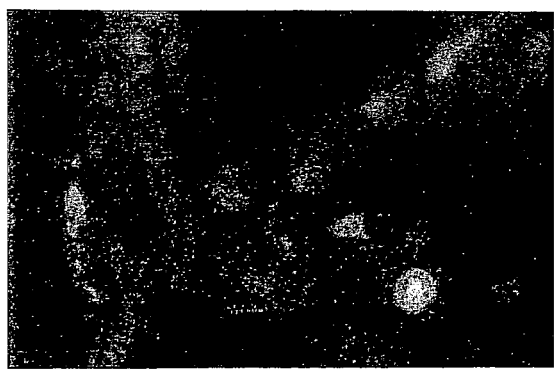
Figure 8:
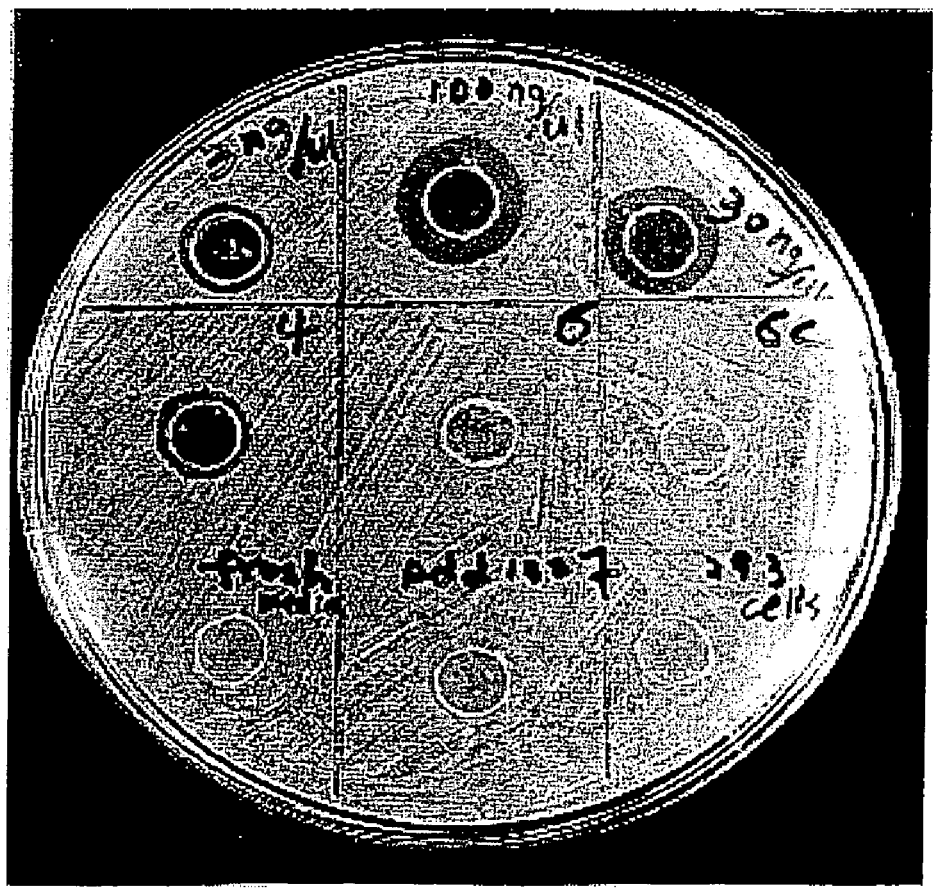
FIG. 8 depicts lysis of *S. aureus* by bioactive lysostaphin produced by 293 cells infected with Ad-hGH-Lys-ΔGLY1-ΔGLY2. Lysostaphin standards were prepared in media. The concentrations were 3 ng/μl, 30 ng/μl and 100 ng/μl. Samples (60 μl) or standards (15 μl) were added to a LB agar plate freshly streaked with *S. aureus*. Results were evaluated following a 12 hour incubation at 370. Top row, from left to right, lysostaphin standards at concentrations of 3, 100, 30 ng/μl; middle row, from left to right: cell culture media of 293 cells infected by Ad-hGH-Lys-ΔGLY1-ΔGLY2 isolates #4 and #6, and by 293 cells infected with parent virus Addl 327. bottom row, from left to right: fresh cell culture media, cell culture media of 293 cells infected by Addl 327, and cell culture media of uninfected 293 cells.

Lysostaphin expression from the four new constructs was evaluated following their transfection into COS-7 cells. The cells were transfected in six-well culture plates, with a $CaPO_4$ precipitation technique (Sambrook et al., *Molecular Cloning: A Laboratory Manual*, Cold Spring Harbor Press, N.Y., 1989, incorporated herein by reference). Following exposure to the plasmid precipitate, cells were washed and then incubated with 1 ml DMEM containing 10% FBS for 48 hr Media was then collected, cleared by centrifugation and stored (−20 C.°). Cell extracts were obtained by freeze/thaw disruption of the cell monolayer with 0.5 ml phosphate buffered saline (PBS). Transfection efficiency was monitored visually by co-transfection with a green fluorescent protein expression plasmid. The plasmid, pCMV-GFP, was constructed by inserting the GFP encoding fragment from pEGFP-NI (Clontech) into pcDNA3. Plasmid DNA used in transfections contained a 9:1 mixture of the test plasmid and pCMV-GFP. Consistently high (>50%) transfection efficiencies were obtained (FIG. 7F).

Figure 5:
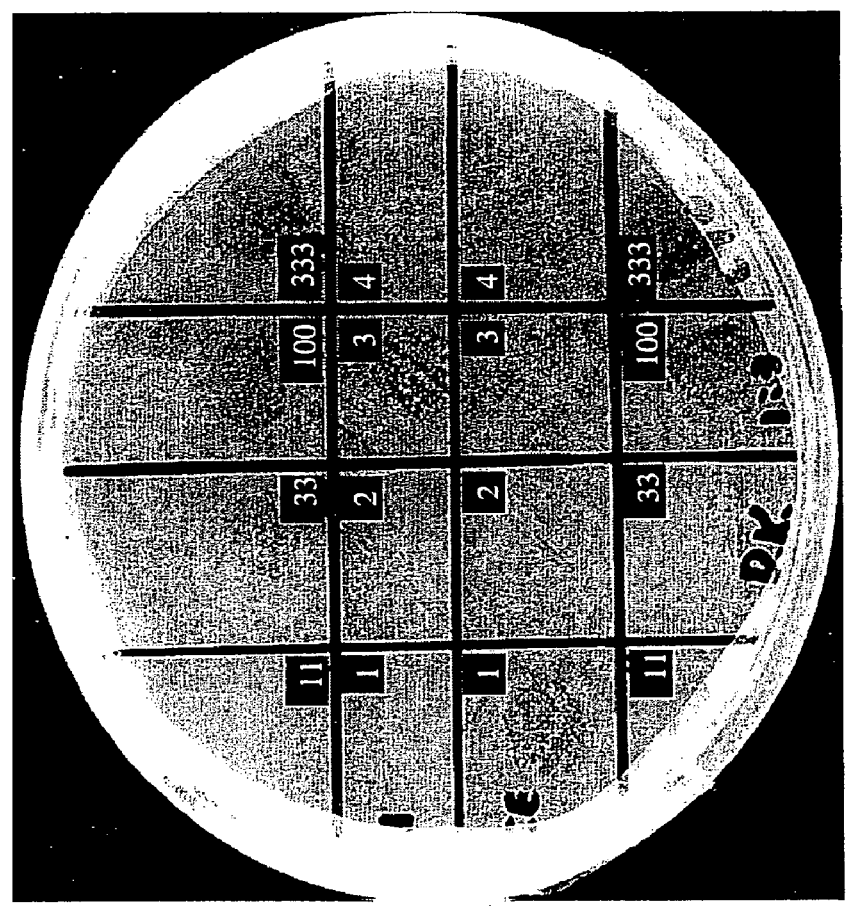
FIG. 5 is a bacterial plate assay for detection of lysis of *S. aureus* (M60) by media or cell extracts from transfected COS-7 cells. Media and cell extracts were obtained 48 hr post transfection with (1) pCMV-Lys, (2) pCMV-hGH-Lys, (3) pCMV-hGH-Lys-ΔGly1-ΔGly2, (4) pCMV-hGH genomic as a control. Conditioned media or cell extracts were lyophilized and resuspended with one third the original volume of H₂O. Top row: Lysostaphin standards at concentrations of 11, 33, 100 or 300 ng/ml in media. Second row: Conditioned media, Third row: cell extracts. Bottom row: Lysostaphin standards that were diluted 1:3 in media, lyophilized, and resuspended with one third the original volume of H₂O.

Cell extracts from COS-7 cells transfected with the signal peptide devoid construct, pCMV-Lys, exhibited bacteriolytic activity using plate assay technique (FIGS. 3 and 5). For the plate assay, aliquots of the cell extract or conditioned media were spotted onto culture plates that had been freshly streaked with *S. aureus* (strain M60). Following an overnight incubation clear lytic zones were observed. We estimated the lysostaphin concentration to be ≈50 ng/ml by comparison with standard preparations containing a commercial lysostaphin preparation (Sigma L-7386). No activity was detected in media, presumably because the lysostaphin gene lacked a signal peptide. No activity was detected in media or cell extracts from cells transfected with a control plasmid, pCMV-hGH. Thus, the COS-7 cells are capable of producing lysostaphin, and it appears to be non-toxic.

Figure 6:
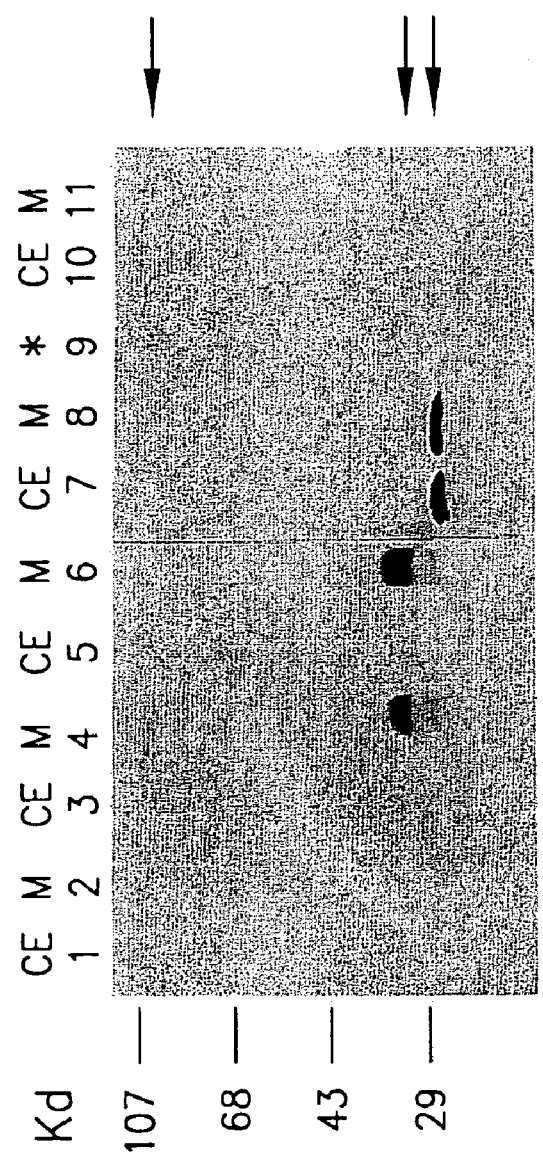
FIG. 6 represents western blot analysis of lysostaphin expressed in transfected COS-7 cells. Proteins were separated on a 12% polyacrylamide-SDS gel, transferred to nitrocellulose membranes and probed with a rabbit anti-lysostaphin polyclonal antibody. Bound antibodies were detected with an alkaline phosphatase-linked second antibody and BCIP/NBT substrate. Molecular size standards are shown on the left. Lanes contain 50 μl cell extract (CE), or media (M), respectively, from cells transfected with: pCMB-hGH as control (lanes 1,2), pCMV-hGH-Lys (lanes 3,4), pCMV-hGH-Lys-ΔGly2 (lanes 5,6), pCMV-hGH with standard lysostaphin protein added to 1 μg/ml (lanes 7,8), Ad-preprolysostaphin (lanes 10,11). Lane 9 (*) contained culture media and Ad-preprolysostaphin as used for infection.

Lysostaphin bioactivity was not detected using the *S. aureus* plate assay, in either media or cell extracts from COS-7 cells transfected with pCMV-hGH-Lys. However, substantial lysostaphin immunoreactivity was observed by western blot assay of media but not extracts of cells transfected with p pCMV-hGH-Lys (FIG. 6, lane 4). The band migrated with an apparent molecular weight of ≈33 Kd, somewhat larger than the lysostaphin standard that migrated at ≈28 Kd. Media samples were estimated to contain ≈200 ng/ml of immunoreactive lysostaphin. To determine if the larger molecular weight of the engineered protein was due to N-linked glycosylation, samples were deglycosylated by overnight incubation with N-glycosidase-F (Boehringer-Mannheim). A clear reduction in the apparent molecular weight of the expressed protein to that of the lysostaphin standard was observed (FIG. 4, lane 5). Thus, addition of the hGH signal peptide region to pCMV-Lys directed the secretion of relatively large quantities of a glycosylated inactivated lysostaphin protein by COS-7 cells. The 26 amino acid signal peptide, which has a predicted molecular weight of 2.7 Kd, was apparently cleaved, as the deglycosylated protein had a similar molecular weight to the lysostaphin standard.

Transfection with the pCMV-hGH-Lys-ΔGly2 construct did not result in the desired increase in activity or size reduction of COS-7 produced lysostaphin. The media, but not cell extracts, obtained from these transfections contained similar levels of similar sized immunoreactive lysostaphin as those resulting from pCMV-hGH-Lys transfections (FIG. 6, lane 6).

Transfection of the eucaryotic cell line, COS-7, with the pCMV-hGH-Lys-ΔGly1-ΔGly2 construct, that encodes a lysostaphin protein in which both N-linked glycosylation sites have been removed reveals bioactive lysostaphin in the culture media but not in the cell extracts (see FIG. 5). Strong, yet indirect evidence for secretion of the protein rather than cell lysis and release into media is found by comparison of results obtained from the signal peptide devoid construct pCMV-Lys, and the new construct containing the hGH signal peptide, pCMV-hGH-Lys. Without the signal peptide, lysostaphin accumulates within the cells such that cell extract, but not media cause bacterial lysis. This media likely does contain some lysostaphin resulting from cell lysis, but the concentration is below the detection limits of our assay. However, with the hGH signal peptide, and the deglycosylation construct, bioactive lysostaphin is detected only in media, not in cell extract. Presumably the cell extract contains an amount of bioactive lysostaphin that is below detection. No bioactivity is observed from cells transfected with the construct containing the hGH signal peptide and the unmodified lysostaphin gene.

Example 2

Adenovirus Mediated Expression of β-galactosidase

A. Propagation of Av1LacZ4

The plasmid Av1LacZ4, (Genetic Therapy Inc; Bethesda, Md.), is a replication deficient, recombinant, human type 5 adenovirus that contains the gene for nuclear targeted β-galactosidase (LacZ) (Smith et al., supra). The E3 region of this adenovirus has been deleted and the β-galactosidase gene replaces the E1a region rendering the virus replication incompetent. Viral stocks were prepared using the 293 packaging cell line (ATCC #CRL-1573). This cell line is a stable transfectant that produces the Ad 5 E1a transcription factor and thus complements the E1a deletion in the recombinant virus. Briefly, confluent 293 cells were infected with the virus and 36 hr later the propagated virus particles recovered by 5 cycles of freeze/thawing. A cleared lysate was obtained by low speed centrifugation, and a purified preparation was obtained following two rounds of CsCl density-gradient ultracentrifugation. The CsCl was removed by extensive dialysis against sterile 10 mM Tris pH 7.4, 1 mM $MgCl_2$, 10% glycerol. Viral stocks were stored at $-70$ C.°. Titres of the viral stocks were determined by plaque assay using 293 cells.

B. Infection of a Ruminant Cell Line with Av1LacZ4

To confirm integrity of our viral stocks and to ensure that the human Ad5 would infect ruminant cells, a bovine mammary epithelial cell line, BME-UV clone E-T2 (Zavizion et al., *In Vitro Cell Dev. Biol. Anim.* 32:138–148, 1996) was exposed to Av1LacZ4 (10 pfu/cell). After 48 hr the cells were fixed and stained for β-galactosidase activity using the X-Gal reagent. The infection was successful (FIG. 7E).

C. Infection of the Goat Mammary Gland In Vivo

Goats were exposed to Av1LacZ4 to evaluate the ability of the human adenovirus to infect the ruminant mammary gland in vivo. Two mature virgin, and three multiparous goats, that had been non-lactating for three months, were infused with the LacZ containing adenovirus. One teat of each goat was infused with 1 ml of a solution (10 mM Tris pH 7.4, 1 mM $MgCl_2$, 10% glycerol) containing Av1 LacZ4 ($1.9 \times 10^{10}$ pfu/ml). The contralateral teat acted as control being infused with vehicle. A similar set of infusions was administered 48 hr later but the concentration of virus was reduced to 0.6 pfu/ml. The animals were euthanized 24 hr later.

Teat tissue and mammary tissue samples adjoining the base of the teat were fixed in 2% paraformaldehyde—020.% glutaraldehyde and processed for detection β-galactosidase activity (Furth et al., *Molecular Biotechnology*, 4:121–127, 1995). Intense blue staining of the entire lining of the teat canal was observed (FIG. 7A). Histological sections revealed that the infection was limited to the luminal cell layer (FIG. 7C). Mammary tissues were also infected (FIG. 7B).

Primary cultures of mammary tissues were prepared by collagenase digestion and plating on plastic culture dishes. After 24 hr incubation in DMEM containing 10% FBS in a 5% $CO_2$ atmosphere, the cultures were fixed and stained with X-Gal. Infected mammary epithelial cells were observed (FIG. 7D). There was no staining visible in tissues or cells from vehicle infused glands.

D. Characterization of Adenoviral-Mediated Transfection of the Goat Mammary Gland In order to continue to explore adenoviral transfection of the goat mammary gland the β-galactosidase-containing adenovirus, Av1LacZ4 is used. These studies are conducted with two, non-lactating multiparous goats/treatment similar to the experiment described above. First, the dose response characteristics using a single infusion of adenovirus is explored. Goats are infected with a single, 1 ml infusions of $1.0 \times 10^{11}$, $1.0 \times 10^{10}$, $1.0 \times 10^9$ and $1.0 \times 10^8$ pfu/ml. Contralateral glands received vehicle alone. These doses are based upon previous results. Mammary secretions are obtained prior to, and at 24 hr and 48 hr post-infusion. The goats are euthanized 48 hr post-infusion. Evaluation of the infections include monitoring animal health (temperature, respiration, rumination, and post-mortem evaluation) and determining SCC and the presence of bacterial infection.

Transfection is evaluated by staining teat and mammary tissues with X-gal reagent and then evaluating them grossly and microscopically. Histopathology is also evaluated. Infusions of $1.9 \times 10^{10}$ and $0.6 \times 10^{10}$ pfu/ml are administered 72 hr and 24 hr prior to euthanasia, respectively. A minor inflammatory response may develop as evidenced by fluid accumulation in the gland and an elevation in somatic cell count. Rectal temperatures are monitored. Secretions are exmined for bacterial contamination. This characterization allows determination of the lower dose of adenovirus that will ameliorate these symptoms, and yet still provide adequate transfection.

E. Adenoviral-Based Transfection of the Goat Mammary Gland with an Engineered Lysostaphin Construct.

Adenoviral-based transfection of the goat mammary gland in vivo has been undertaken as with the Av1LacZ4 infections. Each of two multiparous non-lactating goats were infected in one gland by intramammary teat infusion with the lysostaphin-containing adenovirus. The contralateral gland was infused with the LacZ-containing adenovirus. The goats were euthanized 48 hr post-infusion. Mammary secretions were collected prior to infusion, and at 24 hr and 48 hr post-infusion. Secretions and tissues from the glands were processed as previously described with additional measurements for lysostaphin production and activity as follows.

Secretions from the glands, and extracts prepared from tissue fragments, were assayed for immunoreactive lysostaphin using western blot and an ELISA that have been developed. Prior to assay, sample infranatants were prepared by two sequential centrifugation steps (15 min, 12,000 g, 4 C.°), in which the fluid between the fat layer and pelletable protein and debris was harvested. All secretions were normalized based upon total protein content, determined by a modification of the Lowry method (Nerurkar et al., in Manual of Macrophage Methodoloogy, (H. B. Herscowitz et al, eds.) New York: Marcel Dekker, Inc., pp. 229–246, 1981). Recovery of standard lysostaphin added to samples prior to processing was determined. At 48 hr post-infusion, the secretions collected from the two glands infused with the lysostaphin adenovirus contained 860 ng/ml and 1100 ng/ml, respectively, of lysostaphin. No lysostaphin was detected in the secretions from the contralateral glands infused with the lacZ-adenovirus.

Lysostaphin production is also evaluated in tissue sections processed for immunohistochemistry using our rabbit polyclonal antibody to lysostaphin. Immunohistochemical techniques are currently available. Briefly, formalin fixed tissue is embedded in paraffin, and sectioned (6 μm) by the UVM histology core facility. Slides are then deparaffinized and rehydrated. Endogenous peroxidase are blocked by a 10 min incubation with 0.3% hydrogen peroxide in methanol. Non-specific protein binding is blocked with a 30 min incubation in 10% normal goat serum in 1% BSA-PBS. Sections are be incubated for 60 min with 10 μg/ml of our rabbit polyclonal antibody generated against lysostaphin. Bound antibody is detected with biotinylated goat anti-rabbit IgG (Vector Laboratories, Burlingame, Calif.) subsequently coupled to streptavidin-peroxidase. Then the chromogen, amino ethyl carbazole (AEC) and the substrate (0.6% peroxide) are added to the sections allowing the development of a red color (Zymed Laboratories, San Francisco, Calif.). Negative controls are incubated with the primary antibody in the presence of a 100 fold excess of a lysostaphin.

Methods for adenoviral-based transfection of the lactating goat mammary gland are also available. Briefly, experiments are conducted, similar to those described above, during the sixth week of established lactation. Kids are used to initiate and maintain lactation, but are be replaced by hand milking during the viral infusions. Milk is removed from glands immediately prior to adenoviral infusion. Oxytocin is administered to ensure let-down. One gland is infused with Av1 LacZ4, the other with the lysostaphin containing adenovirus. Initial dose response experiments, conducted with two goats/dose, are undertaken to evaluate transfection during lactation. These experiments are 48 hours in duration. Subsequent longer duration experiments are conducted with a dose determined from previous experiments.

Example 3

Adenovirus Mediated Expression of Lysostaphin

A. Construction of Adenoviruses Containing Lysostaphin Genes

GTI supplied start up quantities of an E3 region deletion mutant (AD5-dl327) of the AD5 adenovirus, and the shuttle plasmid pAvS6 (Smith et al., supra) that was used to construct the recombinant adenoviruses carrying the lysostaphin gene. The Not I-Kpn I fragment of the shuttle plasmid contains the inverted terminal repeat and encapsidation signal from the left end of AD5-dl327, the RSV promoter, a multi-cloning region for insertion of the gene of interest, the SV40 Poly (A+) signal, and Ad5 sequences from nucleotide 3328 to 6246 that serve as a homologous recombination region.

Two shuttle plasmids were constructed. One, named pAvS6-preprolys, was constructed by inserting the 1.5 Kb modified lysostaphin gene from pCMLEM (Williamson et al., 1994) into the pAvS6 shuttle vector. This modified lysostaphin gene contained a Kozak region linked to the preprolysostaphin gene. The other called pAvS6-hGH-Lys-ΔGLY1-ΔGLY2 contained the human growth hormone signal peptide linked to the modified lysostaphin construct which was obtained from pCMV-hGH-Lys-ΔGLY1-ΔGLY2.

The shuttle plasmids, pAvS6-preprolys, and pAvS6-hGH-Lys-ΔGLY1-ΔGLY2 were independently used to generate two recombinant adenoviruses, Ad-preprolys and Ad-hGH-Lys-ΔGLY1-ΔGLY2, respectively. The recombinant viruses were constructed by co-transfection of the linearized shuttle plasmids with the Cla I fragment of Ad5-dl327 into 293 cells. Resulting plaques were purified. Insertion of the lysostaphin genes into the viral genomes was confirmed by polymerase chain reaction.

B. Evaluation of Lysostaphin Production by COS-7 Cells Infected with Ad-Preprolys Near confluent cultures of COS-7 cells were exposed to a cleared cell lysate from 293 cells that had been infected with Ad-preprolys to evaluate lysostaphin production. Samples of culture media and cell extracts were prepared from the infected COS-7 cells 48 hr after infection. Lysostaphin production was evaluated by an SDS-PAGE-western blotting technique using a rabbit polyclonal antibody to lysostaphin (FIG. 3). The antibody was prepared for us by R. Sargent Inc. (Ramona, Calif.) using affinity purified lysostaphin (Sigma L-4402). Samples (50 µl) were denatured by boiling in the presence of a β-mercaptoethanol-containing loading buffer and electrophoresed through a 1.5 mm thick, 12% polyacrylamide gel for 4 hrs (Protean II apparatus; Bio-Rad). Proteins were then transferred to nitrocellulose for immunodetection. Bound anti-lysostaphin antibody was detected with an alkaline phosphatase-linked second antibody (Sigma) and BCIP/NBT reagent (Bio-Rad). Cell extract from Ad-preprolys infected COS-7 cells contained a detectable quantity, of immunoreactive lysostaphin that migrated with an apparent molecular weight of ≈90 Kd (FIG. 3, lane 10). This molecular mass is very similar to that previously observed by Williamson et al. (1994) following introduction of a similar lysostaphin construct using a plasmid based calcium phosphate transfection protocol. The protein is likely preprolysostaphin. Mature lysostaphin migrates with an apparent MW of ≈28 Kd (FIG. 3, lanes 7, 8) The lysostaphin derived from Ad-preprolys infected COS-7 cells was apparently not secreted as it was not detectable in the corresponding media sample (FIG. 3, lane 11). No bioactivity was detected in media or cell extracts from Ad-preprolys infected COS-7 cells.

C. Evaluation of Lysostaphin Production by 293 Cells Infected with Ad-hGH-Lys-ΔGLY1-ΔGLY2

Lysis of *S. aureus* (M60) by bioactive lysostaphin produced by 293 cells infected with Ad-hGH-Lys-□GLY1-□GLY2 was evaluated by plate assay. Samples (60 µl) or standards (15 µl) were added to a LB agar plate freshly streaked with *S. aureus*. Results were evaluated following a 12 hour incubation at 37° C. Lysostaphin standards were prepared in media. The concentrations were 3 ng/µl, 30 ng/µl and 100 ng/µl. Inhibition of *S. aureus* growth was observed by the standard preparations and by culture media obtained from 293 cell cultures that had been infected with Ad-hGH-Lys-ΔGLY1-ΔGLY2. These results are illustrated in FIG. 1.

Example 4

Production and Evaluation of Transgenic Mice Incorporating the Lysostaphin Gene under Control of a Mammary Specific Promoter This model allows assessment of the functionality of the transgene when incorporated into the genome of an animal, determination of toxicity of the transgenic protein to the lactating mammary gland, and assessment of the effects of the transgene on milk production. The antibacterial properties of milk from these animals can also be measured. A variety of mammary gland and lactation specific promoter regions could be used to direct expression of the lysostaphin gene to the lactating mammary gland. These include, but are not limited to, the regulatory sequences of the casein genes, whey acidic protein, and -lactoglobulin. We chose to use the -lactoglobulin regulatory sequence.

The 4.2 Kb 5'-flanking (promoter) region and 2.1 Kb of the 3-flanking region of the ovine-lactoglobulin (BLG) gene (pBJ41) were obtained from Dr. A. J. Clark (Roslin Institute, UK). These components have been used to direct the production of mg/ml concentrations of foreign proteins into the milk of mice (Archibald et al., *Proc. Natl. Acad. Sci. USA* 87,5178–5182, 1990) and sheep (Wright et al., *Bio/technology* 9, 830–834, 1991). The 1.4 Kb modified lysostaphin gene containing the hGH signal peptide was excised from pSec-Lys-G1n2 and inserted into pBJ41 between the 5- and 3-components of the BLG gene. The entire 7.7 Kb fusion gene (BLG-Sec-Lys-Gln2) was then excised and purified for microinjection. Nine founder transgenic mice were produced in the laboratory of Dr. R. J. Wall (USDA-ARS-GEML; Beltsville, Md.) using standard techniques. Five lines of mice have now been established. These mice appear normal, are fertile, and are able to raise offspring. To date, milk has been obtained from F1 mice representing three of the lines. The milk was collected on day 10 of lactation (Maga et al., *J. Dairy Sci.* 78: 2645–2652, 1995). The milk samples were immediately frozen (–80° C.) and then shipped to our laboratory on dry ice.

Figure 9:
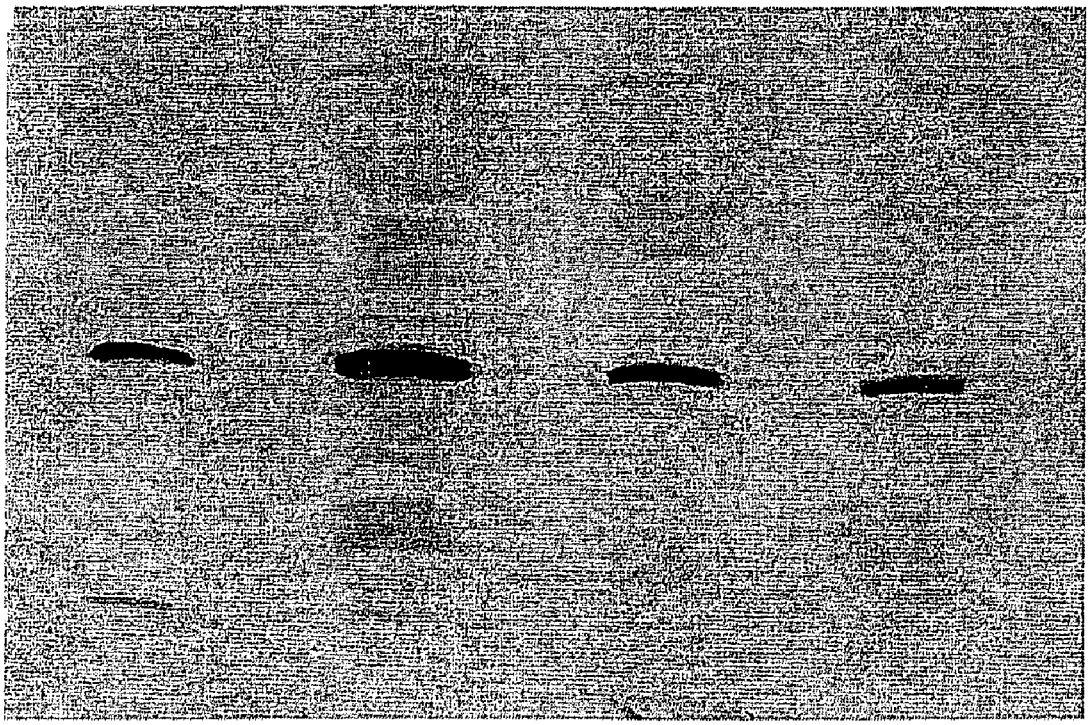
FIG. 9 shows a Western blot of lysostaphin in milk from transgenic mice containing the BLG-Lys-ΔGLY1-ΔGLY2 construct. Lane 1 contains 10 μL of lysostaphin standard (Sigmas 1 μg/μl) in PBS—1% BSA. Lanes 2–4 contain milk samples from three different transgenic mice (10 μl milk diluted 1:10 in PBS—1% BSA) Lysostaphin was not detected in non-transgenic mouse milk.

Milk was analyzed for lysostaphin immunoreactivity as described for cell culture experiments. Prior to analysis milk samples were diluted (1:10) in PBS containing 0.5% BSA, then defatted by centrifugation (15 min, 4, 10,000 g). Western blot analysis of milk from three different BLG-Sec-Lys-Gln2-transgenic mice (#16797, #16796, #16775) revealed a very intense lysostaphin band (FIG. 9). The migration distance appears identical to the lysostaphin standard.

Figure 10:
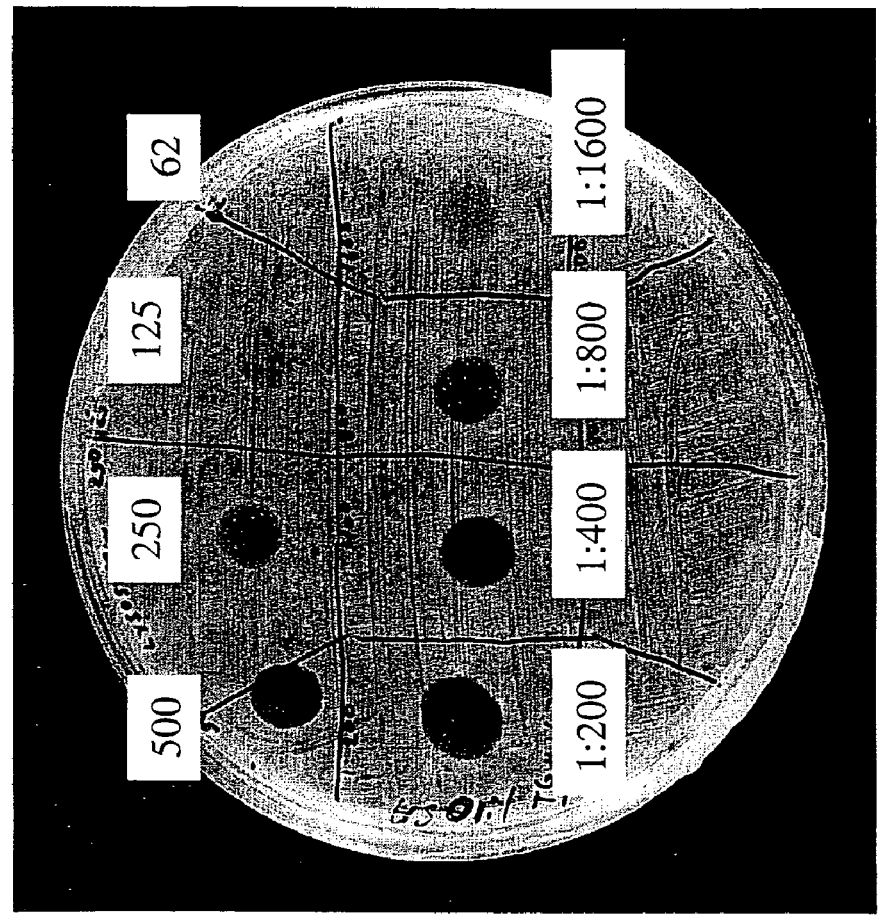
FIG. 10 shows a bacterial plate assay for lysostaphin bioactivity in mouse milk. Milk samples or lysostaphin standards (15 μl) were spotted onto a freshly plated lawn of *S. aureus*, and lytic zones were observed after overnight incubation. Top row, left to right: bacterially derived lysostaphin (Sigmal, 500, 250, 125, 62 ng/ml in PBS-1% BSA Middle row, left to right: skim milk from a BLG-Lys-transgenic mouse (#16755) diluted 1:200, 1:400, 1:800 or 1:1600 in PBS—1% BSA. Bottom row, left to right: skim milk from a non-transgenic mouse diluted 1:200, 1:400, 1:800 1:1600 in PBS—1% BSA.

Milk from another BLG-Sec-Lys-Gln2-transgenic mouse (#16755) contained substantial staphylolytic bioactivity (FIG. 10). The lytic zones that developed from a dilution series of milk indicated that a 1:1,600 dilution of milk contained an amount of bioactivity equivalent to between 125 ng/ml and 250 ng/ml of lysostaphin standard (Sigma).

Example 5

Transgenic Ruminants

The present invention provides transgenic dairy cows containing a modified lysostaphin gene, although the cost and duration of such an endeavor necessitates preliminary experiments using the much less expensive, and more rapid, transgenic mouse model.

A. Production of Non-Rodent Transgenic Animals

Procedures for the production of transgenic non-rodent mammals and other animals have been discussed by others (see Houdebine and Chourrout, supra; Pursel et al., *Science* 244:1281, 1989; and Simms et al., *Bio/Technology,* 6:179, 1988). Such procedures can be applied to an altered gene of the present invention to produce transgenic dairy cows expressing lysostaphin (see Krimpenfort et al., *Biotechnology,* 9:844–847, 1991, incorporated herein by reference). If expression is desirably limited to mammary tissues, a mammary-specific promoter may be employed.

Other Embodiments

One of ordinary skill in the art will readily recognize that the foregoing represents merely a detailed description of certain preferred embodiments of the present invention. Various modifications and alterations of the genes and uses thereof described above can readily be achieved using expretise available in the art, and are within the scope of the following claims.

We claim:

1. An isolated nucleic acid comprising a modified gene, the gene including a sequence that codes for a lysostaphin protein, wherein the lysostaphin protein differs from a naturally occurring version of lysostaphin produced by a host that naturally produces lysostaphin, wherein the encoded protein includes one or more alterations with respect to the naturally occurring version of lysostaphin, and wherein one or more of the alterations disrupts one or more mammalian glycosylation events, so that the non-mammalian protein is produced and secreted by mammalian cells in its active form and kills *Staphylococcus aureus* cells by hydrolyzing pentapeptide links of *Staphylococcus aureus* cell walls.

2. The nucleic acid of claim 1, wherein the modified gene comprises at least one mammalian regulatory sequence operatively linked to the sequence that codes for the lysostaphin protein.

3. The nucleic acid of claim 1 wherein the one or more alterations eliminates one or more glycosylation sites.

4. The nucleic acid of claim 1, wherein the gene comprises a eukaryotic promoter operatively linked to the sequence that codes for the lysostaphin protein.

5. The nucleic acid of claim 4, wherein the eukaryotic promoter is a tissue-specific promoter.

6. The nucleic acid of claim 4, wherein the eukaryotic promoter directs expression of the gene in cells of the mammary gland.

7. The nucleic acid of claim 1, wherein the gene encodes a eukaryotic secretion signal.

8. The nucleic acid of claim 1, wherein the gene encodes a eukaryotic start codon, the Kozak expression start site consensus sequence, or both.

9. The nucleic acid of claim 1, wherein the gene encodes a preprolysostaphin protein.

10. The nucleic acid of claim 1, wherein the gene encodes a prolysostaphin protein.

11. The nucleic acid of claim 1, wherein the sequence is optimized to reflect eukaryotic codon usage.

12. An isolated nucleic acid comprising a gene that encodes a lysostaphin protein, wherein the sequence of the lysostaphin protein contains at most one intact Asn-X-(Ser/Thr) sequence, so that the non-mammalian protein is produced and secreted by mammalian cells in its active form, and wherein the protein kills *Staphylococcus aureus* cells by hydrolyzing pentapeptide links of *Staphylococcus aureus* cell walls.

13. The nucleic acid of claim 12, wherein the gene comprises at least one mammalian regulatory sequence operatively linked to the sequence that codes for the lysostaphin protein.

14. The nucleic acid of claim 12, wherein the gene comprises a eukaryotic promoter operatively linked to the sequence that codes for the lysostaphin protein.

15. The nucleic acid of claim 14, wherein the eukaryotic promoter is a tissue-specific promoter.

16. The nucleic acid of claim 14, wherein the eukaryotic promoter directs expression of the gene in cells of the mammary gland.

17. The nucleic acid of claim 12, wherein the gene encodes a eukaryotic secretion signal.

18. The nucleic acid of claim 12, wherein the gene encodes a eukaryotic start codon, the Kozak expression start site consensus sequence, or both.

19. The nucleic acid of claim 12, wherein the gene encodes a preprolysostaphin protein.

20. The nucleic acid of claim 12, wherein the gene encodes a prolysostaphin protein.

21. The nucleic acid of claim 12, wherein the sequence is optimized to reflect eukaryotic codon usage.

22. An isolated nucleic acid that codes for an active lysostaphin protein encoded by a nucleic acid having a sequence set forth in SEQ ID NO: 3, wherein the active lysostaphin protein has both of its two sites for N-linked glycosylation in mammalian cells (Asn-X-(Ser/Thr)) altered with respect to the wild type lysostaphin protein, or that encodes an active lysostaphin protein differing from that encoded by SEQ ID NO: 3 in that only one of the sites for N-linked glycosylation is altered with respect to the wild type lysostaphin protein, wherein the active lysostaphin protein kills *Staphylococcus aureus* cells by hydrolyzing pentapeptide links of *Staphylococcus aureus* cell walls.

23. The isolated nucleic acid of claim 22, wherein the nucleic acid codes for an active lysostaphin in which the Asn residue in either or both of the sites for N-linked glycosylation is deleted or replaced by a different amino acid.

24. The isolated nucleic acid of claim 23, wherein the Asn residue in either or both of the sites for N-linked glycosylation is replaced by Gln.

25. The isolated nucleic acid of claim 22, comprising SEQ ID NO: 3 or a variant thereof in which only one of the two Asn codons in the sites for N-linked glycosylation is altered relative to the wild type sequence.

26. The isolated nucleic acid of claim 22, which encodes an active lysostaphin protein identical to the protein encoded by SEQ ID NO: 3 except only one of the sites for N-linked glycosylation is altered with respect to the wild type lysostaphin protein.

* * * * *